(12) United States Patent
Richlen et al.

(10) Patent No.: US 8,079,994 B2
(45) Date of Patent: Dec. 20, 2011

(54) DISPOSABLE ABSORBENT ARTICLES HAVING GENDER-SPECIFIC CONTAINMENT FLAPS

(75) Inventors: Sandra Ann Richlen, Black Creek, WI (US); Amanda Jean Simon, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 493 days.

(21) Appl. No.: 12/148,384

(22) Filed: Apr. 18, 2008

(65) Prior Publication Data
US 2009/0264851 A1 Oct. 22, 2009

(51) Int. Cl.
*A61F 13/15* (2006.01)
(52) U.S. Cl. ......... 604/385.28; 604/385.01; 604/385.24; 604/385.04
(58) Field of Classification Search ............. 604/385.01, 604/385.28, 385.24, 385.04
See application file for complete search history.

(56) References Cited

U.S. PATENT DOCUMENTS

| | | | |
|---|---|---|---|
| 3,559,648 A | 2/1971 | Mason, Jr. | |
| 3,766,922 A | 10/1973 | Krusko | |
| 3,849,241 A | 11/1974 | Butin et al. | |
| 3,926,189 A | 12/1975 | Taylor | |
| 4,037,602 A | 7/1977 | Hawthorne | |
| 4,704,116 A | 11/1987 | Enloe | |
| 4,846,825 A | 7/1989 | Enloe et al. | |
| 4,906,243 A | 3/1990 | Dravland | |
| 4,938,756 A | 7/1990 | Salek | |
| 4,950,263 A | 8/1990 | Lewis | |
| 5,021,051 A * | 6/1991 | Hiuke | 604/385.27 |
| 5,213,881 A | 5/1993 | Timmons et al. | |
| 5,236,428 A | 8/1993 | Zajaczkowski | |
| 5,554,142 A | 9/1996 | Dreier et al. | |
| 5,672,166 A | 9/1997 | Vandemoortele | |
| 5,690,627 A | 11/1997 | Clear et al. | |
| 5,814,035 A | 9/1998 | Gryskiewicz et al. | |

(Continued)

FOREIGN PATENT DOCUMENTS
DE 298 14 465 U1 12/1998
(Continued)

OTHER PUBLICATIONS

"Humanicare International, Inc.," gender-specific incontinence care products, Internet web site "http://www.humanicare.com/consumers.html", viewed prior to Oct. 14, 2008, 1 page.

*Primary Examiner* — Jacqueline F Stephens
(74) *Attorney, Agent, or Firm* — H. Michael Kubicki

(57) ABSTRACT

In one aspect, the present invention relates to an array of gender-specific disposable absorbent articles having gender-specific containment flaps. In one embodiment, the array of articles comprises a first disposable absorbent article adapted to be worn by males, and a second absorbent article adapted to be worn by females. The first disposable absorbent article comprises a first pair of containment flaps, and the second disposable absorbent article comprises a second pair of containment flaps. The first pair of containment flaps differs from the second pair of containment flaps in at least one structural feature. In particular embodiments, the structural feature that differs is selected from the group consisting of flap active length, flap active-portion longitudinal position, flap tension, flap height, distal-to-distal spacing, and proximal-to-proximal spacing. In another aspect, the present invention pertains to a method of marketing gender-specific absorbent articles having gender-specific containment flaps.

16 Claims, 9 Drawing Sheets

U.S. PATENT DOCUMENTS

| | | | |
|---|---|---|---|
| 5,830,202 | A | 11/1998 | Bogdanski et al. |
| 5,895,382 | A | 4/1999 | Popp et al. |
| 5,993,433 | A | 11/1999 | St. Louis et al. |
| 6,017,336 | A | 1/2000 | Sauer |
| 6,121,510 | A | 9/2000 | Sauer |
| 6,478,786 | B1 | 11/2002 | Glaug et al. |
| 6,488,670 | B1 | 12/2002 | Schild et al. |
| 6,607,515 | B2 | 8/2003 | Glaug et al. |
| 6,648,870 | B2 | 11/2003 | Itoh et al. |
| 6,797,858 | B2 | 9/2004 | Erdman |
| 6,863,665 | B2 | 3/2005 | Rosch et al. |
| 2002/0072728 | A1 | 6/2002 | Shinohara et al. |
| 2003/0093045 | A1 | 5/2003 | Erdman |
| 2003/0093050 | A1 | 5/2003 | Baker |
| 2003/0114808 | A1 | 6/2003 | Underhill et al. |
| 2003/0114814 | A1 | 6/2003 | Baker et al. |
| 2003/0114827 | A1 | 6/2003 | Peterson |
| 2003/0120244 | A1 | 6/2003 | Johnson |
| 2003/0130643 | A1 | 7/2003 | Drevik et al. |
| 2003/0225384 | A1 | 12/2003 | Zenker et al. |
| 2004/0019338 | A1 | 1/2004 | Litvay et al. |
| 2004/0097897 | A1 | 5/2004 | Ronn et al. |
| 2004/0122410 | A1 | 6/2004 | Itoh et al. |
| 2004/0143231 | A1 | 7/2004 | Nair et al. |
| 2004/0256048 | A1 | 12/2004 | Owen |
| 2005/0010188 | A1 | 1/2005 | Glaug et al. |
| 2005/0038400 | A1 | 2/2005 | Poruthoor |
| 2005/0101929 | A1 | 5/2005 | Waksmundzki et al. |
| 2005/0109442 | A1 | 5/2005 | Neubauer et al. |
| 2005/0256489 | A1 | 11/2005 | Sawyer et al. |
| 2005/0256757 | A1 | 11/2005 | Sierra et al. |
| 2005/0256758 | A1 | 11/2005 | Sierra et al. |
| 2006/0004342 | A1 | 1/2006 | Sawyer et al. |
| 2007/0038195 | A1 | 2/2007 | Fuchs et al. |
| 2007/0073262 | A1 | 3/2007 | Babusik et al. |
| 2007/0233027 | A1 | 10/2007 | Roe et al. |
| 2008/0071239 | A1 | 3/2008 | Nandrea et al. |
| 2008/0275415 | A1 | 11/2008 | Wheeler et al. |

FOREIGN PATENT DOCUMENTS

| | | |
|---|---|---|
| EP | 1 024 772 B1 | 6/2005 |
| EP | 0 797 423 B1 | 8/2006 |
| WO | WO 89/00037 A1 | 1/1989 |
| WO | WO 98/16179 A1 | 4/1998 |
| WO | WO 2005/018518 A1 | 3/2005 |
| WO | WO 2007/008125 A1 | 1/2007 |

* cited by examiner

DISPOSABLE ABSORBENT ARTICLES HAVING GENDER-SPECIFIC CONTAINMENT FLAPS

BACKGROUND

People rely on disposable absorbent products in their everyday lives, including such articles as adult incontinence products, enuresis pants, training pants, and diapers. Many manufacturers seek to better meet the needs of users of such products. Some manufacturers, for example, have sought to develop products that absorb better. Others have sought to improve fit. Still others have sought to reduce leakage.

Men and women have different body compositions (e.g., percentage of body mass consisting of muscle), different skeletal structures, and age differently. As men get older they tend to lose muscle mass in their legs, resulting in thinner legs. In fact, the circumference of the leg of a typical male user of an adult-incontinence article may actually be smaller than the circumference of the leg of a typical female user of an adult-incontinence article—a counterintuitive finding. Also, for anatomical reasons, men typically release urine at a location further toward the front of the body, while women release urine at a location generally lower on the body compared to men. Furthermore, the shape of a man's hips and groin area is different from a woman's hips and groin area.

We are not aware of product designs, product lines, or ways of marketing that address these and other differing body characteristics of men and women who use disposable adult-incontinence products.

One feature that is important to users is the ability of the article to minimize leakage of fluid, such as urine. To assist in minimizing leakage, disposable absorbent articles may employ a pair of containment flaps that are configured to provide a barrier to the transverse flow of body exudates. In common configurations, one or more flap elastic members are operatively joined with each containment flap to elasticize the flaps. The elasticized containment flaps define an unattached edge which assumes an upright, generally perpendicular configuration, which may form a seal against the wearer's body. The opposing end of the flap is attached to the article. Exemplary constructions and arrangements for containment flaps are generally described, for example, in U.S. Pat. No. 4,704,116 issued Nov. 3, 1987 to Enloe.

While containment flaps can be used in many types of disposable absorbent articles, including training pants, enuresis pants, diapers, adult diapers, and adult pull-on style disposable absorbent underwear, containment flaps have not heretofore been commonly used in adult pull-on style disposable absorbent underwear. Moreover, although the prior art is replete with attempts to vary the construction of containment flaps to improve their performance generally, no attempt has been made to construct containment flaps in a way that addresses the differing body characteristics of men and women who use disposable adult-incontinence products.

SUMMARY

In one aspect, the present invention pertains to an array of gender-specific disposable absorbent articles having gender-specific containment flaps. In one embodiment, the array of articles comprises a first disposable absorbent article adapted to be worn by males, and a second absorbent article adapted to be worn by females. The first disposable absorbent article comprises a first pair of containment flaps, and the second disposable absorbent article comprises a second pair of containment flaps. The first pair of containment flaps differs from the second pair of containment flaps in at least one structural feature. In particular embodiments, the structural feature that differs is selected from the group consisting of flap active length, flap active-portion longitudinal position, flap tension, flap height, distal-to-distal spacing, and proximal-to-proximal spacing. In particular embodiments, the difference in structural feature between the first pair of containment flaps and the second pair of containment flaps is selected from the group consisting of: the first active flap length being greater than the second flap active length, the first flap active-portion longitudinal position being further forward than the second flap active-portion longitudinal position, the first flap tension being lower than the second flap tension, the first flap height being greater than the second flap height, the first distal-to-distal spacing being greater than the second distal-to-distal spacing, and the first proximal-to-proximal spacing being greater than the second proximal-to-proximal spacing.

In another aspect, the present invention pertains to a method of marketing gender-specific absorbent articles. In one embodiment, the method includes providing an array of gender-specific absorbent articles comprising a first disposable absorbent article adapted to be worn by males, and a second absorbent article adapted to be worn by females. The first disposable absorbent article comprises a first pair of containment flaps, and the second disposable absorbent article comprises a second pair of containment flaps. The first and second set of containment flaps differ in some structural respect, such as, for example, in one or more of the manners described above. In particular embodiments, the method additionally comprises simultaneously offering for sale the first and second disposable absorbent articles.

In still another aspect, the present invention pertains to an array of gender-specific disposable absorbent articles having both gender-specific containment flaps as well as at least one additional gender-specific feature. The following paragraphs summarize certain versions of arrays of absorbent articles that include such additional gender-specific features.

One such representative version is an array of disposable adult-incontinence articles, the array comprising: a first disposable adult-incontinence article having a first anterior length, wherein the first article is adapted to be worn by women; and a second disposable adult-incontinence article having a second anterior length, wherein the second article is adapted to be worn by men, and wherein the first anterior length is less than the second anterior length. For purposes of this application, the term "anterior length" refers to the shortest distance between the waist-opening front edge and the leg-opening front edge.

Another such representative version is an array of disposable incontinence articles, the array comprising: a first disposable adult-incontinence article having a first leg-opening front edge, wherein the first article is adapted to be worn by women; and a second disposable adult-incontinence article having a second leg-opening front edge, wherein the second article is adapted to be worn by men, and wherein the first leg-opening front edge is more convex toward the waist-opening front edge than the second leg-opening front edge. That is, the boundary defined by the first leg-opening front edge of the article adapted to be worn by women curves more toward the waist-opening front edge (and away from the open space bounded or partially bounded by the leg-opening edges) compared to the boundary defined by the second leg-opening front edge of the article adapted to be worn by men. For purposes of this application, a women's article having this feature comprises a leg-opening front edge having (or, alternatively, establishing a boundary having) a greater convexity compared to the leg-opening front edge of the corresponding men's article.

Another such representative version is an array of disposable incontinence articles, the array comprising: a first disposable adult-incontinence article having a first leg-opening back edge, wherein the first article is adapted to be worn by women; and a second disposable adult-incontinence article having a second leg-opening back edge, wherein the second article is adapted to be worn by men, and wherein the first leg-opening back edge is more concave toward the waist-opening back edge than the second leg-opening back edge. That is, the boundary defined by the first leg-opening back edge of the article adapted to be worn by women curves more away from the waist-opening back edge (and toward the open space bounded or partially bounded by the leg-opening edges) compared to the boundary defined by the second leg-opening back edge of the article adapted to be worn by men. For purposes of this application, a women's article having this feature comprises a leg-opening back edge having (or, alternatively, establishing a boundary having) a greater concavity compared to the leg-opening back edge of the corresponding men's article.

Another such representative version is an array of disposable adult-incontinence articles, the array comprising: a first disposable adult-incontinence article having a first crotch width, wherein the first article is adapted to be worn by women; and a second disposable adult-incontinence article having a second crotch width, wherein the second article is adapted to be worn by men; and wherein the first crotch width is less than the second crotch width. For purposes of this application, the term "crotch width" refers to the shortest distance between the outside boundaries of the opposing, elastic members closest to the opposing leg-opening side edges. For example, if three elastic strands are employed near each leg-opening side edge, then "crotch width" equates to the shortest distance between: (1) of the three elastic strands proximate to a first leg-opening side edge, the outside boundary of that strand closest to the first leg-opening side edge; and (2) of the three elastic strands proximate to the opposing, second leg-opening side edge, the outside boundary of that strand closest to the opposing, second leg-opening side edge.

Another such representative version is an array of disposable adult-incontinence articles, the array comprising: a first disposable adult-incontinence article having a first gasket width, wherein the first article is adapted to be worn by women; and a second disposable adult-incontinence article having a second gasket width, wherein the second article is adapted to be worn by men; and wherein the first gasket width is less than the second gasket width. For purposes of this application, the term "gasket width" refers to, in the crotch portion, the distance, along a line bisecting the middle of the leg-opening side edges in a transverse direction parallel to the waist-opening edges (see FIGS. 1 and 2 and accompanying text), between a side edge of the absorbent core (e.g., a fluff/superabsorbent core) and the outside boundary of the elastic member closest to the nearest, leg-opening side edge If, as is likely, the absorbent core, such as a core comprising fluff and superabsorbent, is disposed between a liquid-permeable, body-facing liner and a liquid-impermeable outer cover (as with an absorbent insert or assembly comprising an absorbent core sandwiched between a liner and outer cover), then the side edge of the absorbent core is located at the boundary of the fluff/superabsorbent core, not at the boundary of any substrate that helps encase and extends beyond the absorbent core.

Another such representative version is an array of disposable adult-incontinence articles, the array comprising: a first disposable adult-incontinence article having a first leg-opening perimeter, wherein the first article is adapted to be worn by women; and a second disposable adult-incontinence article having a second leg-opening perimeter, wherein the second article is adapted to be worn by men; and wherein the first leg-opening perimeter is greater than the second leg-opening perimeter. For purposes of this application, the term "leg-opening perimeter" refers to the perimeter of a leg opening in a substantially flat, laid-open, disposable adult-incontinence article. The exemplary articles displayed in FIGS. 1 and 2 are in a substantially flat, laid-open condition.

Another such representative version is an array of disposable adult-incontinence articles, the array comprising: a first disposable adult-incontinence article having a first graphic disposed thereon, wherein the first article is adapted to be worn by women; and a second disposable adult-incontinence article having a second graphic disposed thereon, wherein the second article is adapted to be worn by men; and wherein the first graphic is different than the second graphic. In one exemplary embodiment, the first and second graphic comprise one or more stripes disposed on material proximate to the waist portion of the articles, but of a different color (e.g., one or more blue stripes on the article adapted to be worn by men; and one or more pink stripes on the article adapted to be worn by women). Of course, such graphics may be employed in combination with one or more of the inventive features discussed above.

Another such representative version is an array of disposable adult-incontinence articles comprising one or more of the gender-specific features discussed above, with the first disposable adult-incontinence article further comprising an absorbent having a first waist/absorbent distance, wherein the first article is adapted to be worn by women; and a second disposable adult-incontinence article having a second waist/absorbent distance, wherein the second article is adapted to be worn by men; and wherein the first waist/absorbent distance is more than the second waist/absorbent distance. The term "waist/absorbent distance" refers to the minimum distance between the front edge of the waist opening and front edge of the absorbent core. Again, as discussed above, the edge of the absorbent core refers to, for example, the edge of a fluff/superabsorbent core (not the edge of substrates that help contain the core if, as may be the case, the edge of these substrates extend beyond the boundary of the absorbent core itself).

Another such representative version is an array of disposable adult-incontinence articles comprising one or more of the dimensional (e.g., those inventive features directed to a length, width, distance, or other such measurement) or ornamental (e.g., those inventive features directed to disposing a graphic on an article) gender-specific features discussed above, with the first disposable adult-incontinence article further comprising an absorbent core having a first frontal area, wherein the first article is adapted to be worn by women; and a second disposable adult-incontinence article having an absorbent core having a second frontal area, wherein the second article is adapted to be worn by men; and wherein the first frontal area is less than the second frontal area. The term "frontal area," when describing the absorbent core (e.g., a fluff/superabsorbent core), refers to the area of the body-facing surface of the absorbent core forward of an imaginary transverse line bisecting the article, with area determined when the article comprising the absorbent core is in a substantially flat, laid-open position (e.g., for some articles, the substantially flat, laid-open position generally corresponds to an hourglass-like shape). For example, if an article is in a substantially flat, laid-open position, and has an hourglass-like shape like those versions depicted in FIGS. 1 and 2 (and which have a shape generally analogous to the capital letter "I"), an imaginary transverse line would be a horizontal line halfway between the waist-opening front edge and the waist-opening back edge (i.e., the imaginary transverse line would be a horizontal line half-way between the upper and lower horizontal lines that make up the letter "I").

Another such representative version is an array of disposable adult-incontinence articles comprising one or more of the dimensional (e.g., those inventive features directed to a length, width, distance, or other such measurement) or ornamental (e.g., those inventive features directed to disposing a graphic on an article) gender-specific features discussed above, with the first disposable adult-incontinence article further comprising an absorbent core having a first frontal transverse span, wherein the first article is adapted to be worn by women; and a second disposable adult-incontinence article having an absorbent core having a second frontal transverse span, wherein the second article is adapted to be worn by men; and wherein the first frontal transverse span is less than the second frontal transverse span. The term "frontal transverse span," when describing the absorbent core (e.g., a fluff/superabsorbent core), refers to the longest distance, in a transverse direction parallel to the waist-opening edges (see FIGS. 1 and 2 and accompanying text), between the opposing, longitudinal edges of the absorbent core forward of an imaginary transverse line bisecting the article in a substantially flat, laid-open position (e.g., for many articles, the substantially flat, laid-open position generally corresponds to a hourglass-like shape).

Another such representative version of the invention is an array of disposable adult-incontinence articles comprising one or more of the inventive dimensional (e.g., those inventive features directed to a length, width, distance, or other such measurement), ornamental (e.g., those inventive features directed to disposing a graphic on an article) or other gender-specific features discussed above, with the first disposable adult-incontinence article contained in a first package having a first statement disposed thereon, wherein the first article is adapted to be worn by women; and a second disposable adult-incontinence article contained in a second package having a second statement disposed thereon, wherein the second article is adapted to be worn by men; wherein the first statement associates the article with use by women and the second statement associates the article with use by men.

In another representative version of the invention, a gender-specific array of disposable, adult-incontinence articles comprises a gender-specific, disposable, adult-incontinence article that includes a pair of containment flaps including a gender-specific structural feature, and a unisex disposable, adult-incontinence article that includes a second pair of containment flaps. In other words, rather than a comparison being made between an article adapted to be worn by men and an article adapted to be worn by women, the comparison is made between either: (1) an article adapted to be worn by women and a unisex article; or (2) an article adapted to be worn by men and a unisex article. "Unisex" refers to an article that can be worn by either a man or a woman. While the comparison is being made between a unisex article and either an article adapted to be worn by a man or an article adapted to be worn by a women, the relationships described above still hold, with the exception being that a unisex article is substituted for the gender-specific article not present in the array. In other words, if the array was made up of a disposable, adult-incontinence article adapted to be worn by women, and a unisex article (and therefore an article adapted to be worn by men is absent from the array), then, for example, the women's article may comprise a pair of containment flaps having one or more structural features adapted for use in a female absorbent article. If, on the other hand, the array is made up of a disposable, adult-incontinence article adapted to be worn by men, and a unisex article (and therefore an article adapted to be worn by women is absent from the array), then, for example, the man's article might have a pair of containment flaps having one or more structural features adapted for use in a male absorbent article.

For purposes of this application, "fit features" refer to one or more of anterior length, shape of leg-opening front edge (i.e., degree of convexity of said edge), shape of leg-opening back edge (i.e., degree of concavity of said edge), leg-opening perimeter, and gasket width. Also, for purposes of this application, "leg-opening features" refers to one or more of anterior length, shape of leg-opening front edge, shape of leg-opening back edge, and leg-opening perimeter.

Other versions of absorbent articles having additional gender-specific features (i.e., additional to the gender-specific flaps) include a fit feature adapted for a specific gender. Still other versions comprise various combinations of those features denominated as fit features, and which are adapted for a specific gender.

Other versions of absorbent articles having additional gender-specific features (i.e., additional to the gender-specific flaps) include a leg-opening feature adapted for a specific gender. Still other versions comprise various combinations of those features denominated as leg-opening features, and which are adapted for a specific gender.

DRAWINGS

FIG. 8a is a cross-sectional view of the absorbent assembly of FIG. 7 taken along line 8a-8a.

DESCRIPTION OF PARTICULAR EMBODIMENTS

Figure 1:
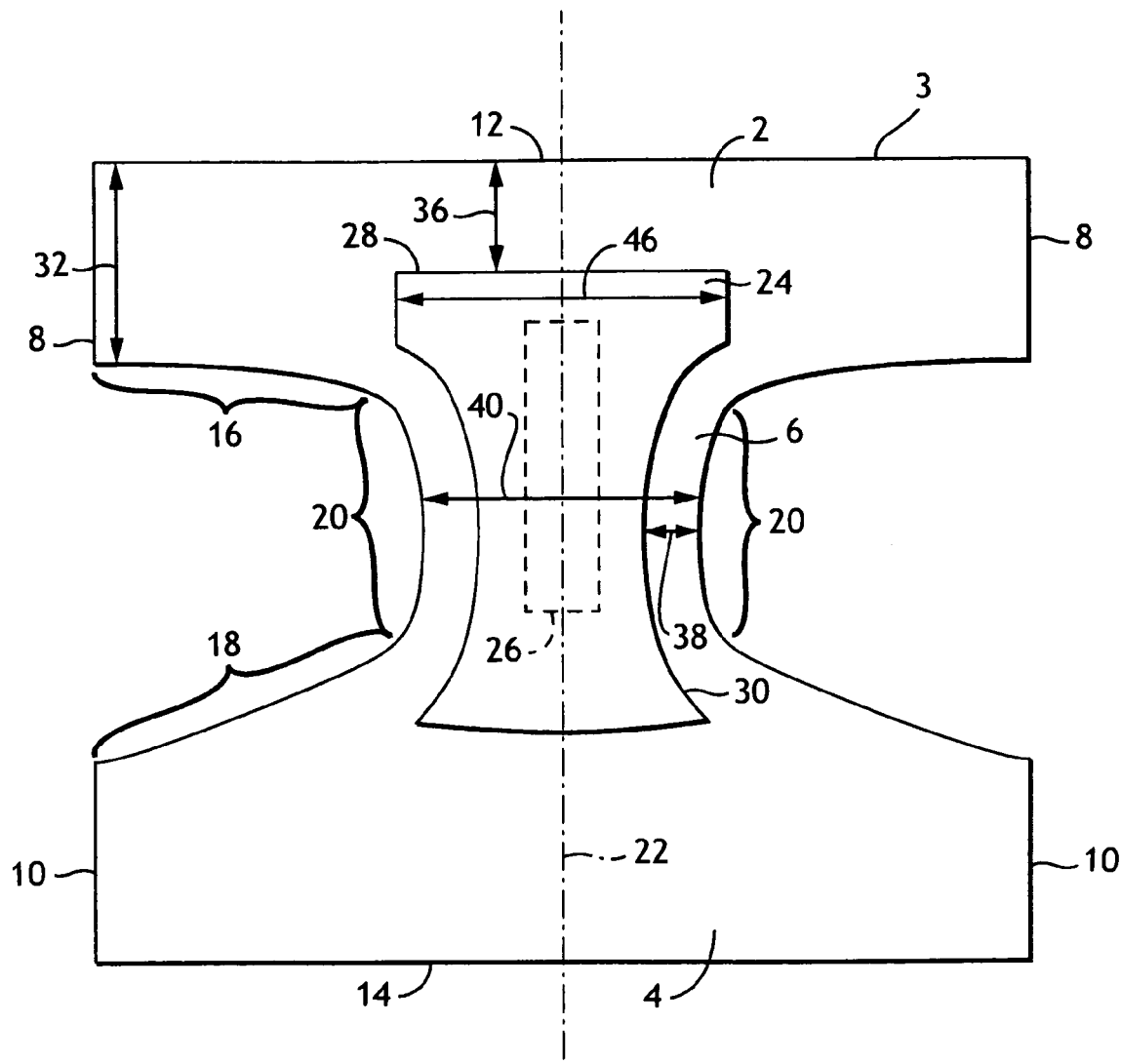
FIG. 1 depicts one representative example of a disposable adult-incontinence article adapted to be worn by a man.

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Fiber" refers to a continuous or discontinuous member having a high ratio of length to diameter or width. Thus, a fiber may be a filament, a thread, a strand, a yarn, or any other member or combination of these members.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

These terms may be defined with additional language elsewhere in the specification.

It should be noted that a number of the features in this invention implicate a measurement of length. In many cases a simple rule may be used to measure the distance from one edge to another. Of course more sophisticated techniques may be used (e.g., when measuring the perimeter of the leg opening, which can comprise a series of curves). For example, photomicrographs can be prepared and analyzed. Such images could be digitized and appropriate algorithms used to measure length. Alternatively, mechanical devices may be used. Because many of the inventive versions are directed to arrays comprising two products, it is important that the same measurement technique be used when comparing features (e.g., anterior length) of two products in an array.

Generally, the gender-specific disposable articles (such as, e.g., adult incontinence articles) of the present invention are manufactured using methods and processes known in the art, but configured to produce one or more features in the article adapted to be worn by women that are different than one or more features in the article adapted to be worn by men. As noted above, analysis of the physiological characteristics of men and women resulted in gender-specific designs, the features of which are described in more detail in the following paragraphs.

FIG. 1 depicts an exemplary version of a disposable, adult-incontinence article adapted to be worn by a man. FIG. 1 presents a plan view of a substantially flat, laid-open article before attachment of the side edges of the front portion to the side edges of the back portion to form an article having a waist opening and two leg openings. The front portion, back portion, and their respective side edges are identified below.

As noted above, the article includes a front portion 2 and a back portion 4. The front portion and back portion are interconnected by a crotch portion 6. Generally the term "chassis" is used to refer to the combination comprising a front portion, a back portion, and a crotch portion connecting said front portion to said back portion. The front portion has two side edges 8 and the back portion has two side edges 10. When assembling the article, the side edges 8 are attached to the side edges 10 to form a shape similar to that of underwear and having a waist opening and two leg openings. If desired, the side edges may be releasably engaged to one another (e.g., by using mechanical fasteners such as hook-and-loop-type materials; adhesives; etc.). Also, the side edges of the front and back portions need not be attached directly to one another, but may be attached to one or more intermediate elements (e.g., side panels—not shown in the figures).

The front portion also has a waist-opening front edge 12, and the back portion has a waist-opening back edge 14. When the side edges are joined to one another, the waist-opening edges are connected to form a perimeter that typically fits around the lower torso of a user.

For purposes of this application, the edges defining the leg opening are categorized as including a leg-opening front edge 16, a leg-opening back edge 18, and a leg-opening side edge 20. Typically, a major portion of the leg-opening side edge runs somewhat parallel to an imaginary longitudinal centerline 22 running from the back to the front of the article. Major portions of the leg-opening front and back edges will typically not run parallel to the longitudinal centerline. The leg-opening is categorized in this way to help distinguish certain features of gender-specific articles from one another, as discussed below.

The article will typically include an absorbent core 24. In the depicted representative example, the absorbent core includes fluff (not shown), super absorbent material (not shown), and an optional surge material 26 adapted to help rapidly take in and distribute urine for absorption by the fluff/superabsorbent material. The absorbent core includes an absorbent core front edge 28, and absorbent core side edges 30. For those articles made by attaching an absorbent assembly or absorbent insert to, for example, an hourglass-like substrate, with the assembly comprising an absorbent core sandwiched between a liquid-permeable, body-side liner, and a liquid-impermeable garment-side outer cover, the liner, outer cover, or both may extend beyond the edge of the absorbent core itself. For example, in some articles, the liner and outer cover (i.e., the backsheet of the absorbent core insert) are attached to one another around the perimeter of the absorbent core contained therein, and the area of attachment of these materials may form a flexible flange extending beyond the edge of the absorbent core. Such a flange is not depicted in FIG. 1 or FIG. 2.

These various edges help further define one or more distances that can vary between a disposable, adult-incontinence article adapted to be worn by a man, and a disposable, adult-incontinence article adapted to be worn by a woman. As noted earlier, the anterior length 32 is the shortest distance between the leg-opening front edge 16 and the waist-opening front edge 12. It should be noted that for purposes of clearly depicting the anterior length in FIG. 1, the two-headed arrow representing this distance is slightly offset from one of the side edges 8 of the front portion. If, however, this side edge corresponded to the shortest distance between the leg-opening front edge 16 and the waist-opening front edge 12, then the anterior length 32 would actually overlay the side edge 8.

The waist/absorbent distance 36 is the shortest distance between the absorbent core front edge 28 and the waist-opening front edge 12.

The gasket width 38 is the distance, in the crotch portion, along a line bisecting the middle of the leg-opening side edges and in a transverse direction, between the absorbent core side edge 30 and the outer boundary of the elastic member closest to leg-opening side edge 20. It should be noted that in FIG. 1, the two-headed arrow representing this distance touches the leg-opening side edge 20 because of the difficulty in representing the small distances typically characterizing the length between the outer boundary of the elastic member closest to the side edge, and the side edge itself. Of course, in reality, if the outer boundary of the elastic member closest to the leg-opening side edge is inward of the side edge, as is likely the case, then gasket width is measured to the outer boundary of the elastic member—not to the side edge itself.

The crotch width 40 is defined as the shortest distance between the outside boundaries of the opposing, elastic members closest to the opposing leg-opening side edges 20. It should be noted that in FIG. 1, the two-headed arrow representing this distance touches the leg-opening side edges 20 because of the difficulty in representing the small distances typically characterizing the length between the outer boundary of the elastic member closest to the side edge, and the side edge itself.

The frontal area of the absorbent core 24 corresponds to the body-facing surface area of that region of the absorbent core between an imaginary transverse line approximately bisecting the article when in a substantially flat, laid-open position (this imaginary line is not shown in FIGS. 1 and 2, but would approximately overlay the double-headed arrow designated as "40") and the waist-opening front edge.

The frontal transverse span or distance 46 corresponds to the longest distance, in a transverse direction, between the opposing, longitudinal side edges 30 of the absorbent core, for that portion of the absorbent core forward of a location between an imaginary transverse line bisecting the article in a substantially flat, laid-open position and the waist-opening front edge (the location of which, for the depicted, representative embodiment, is discussed in the previous paragraph). It should also be noted that, for the depicted embodiment, the side edges 30 of the absorbent core establish a somewhat complex boundary, with a curvilinear portion in the crotch region, and a linear portion in the front region, with each linear portion extending in a substantially perpendicular fashion toward the front edge of the absorbent core.

Figure 2:
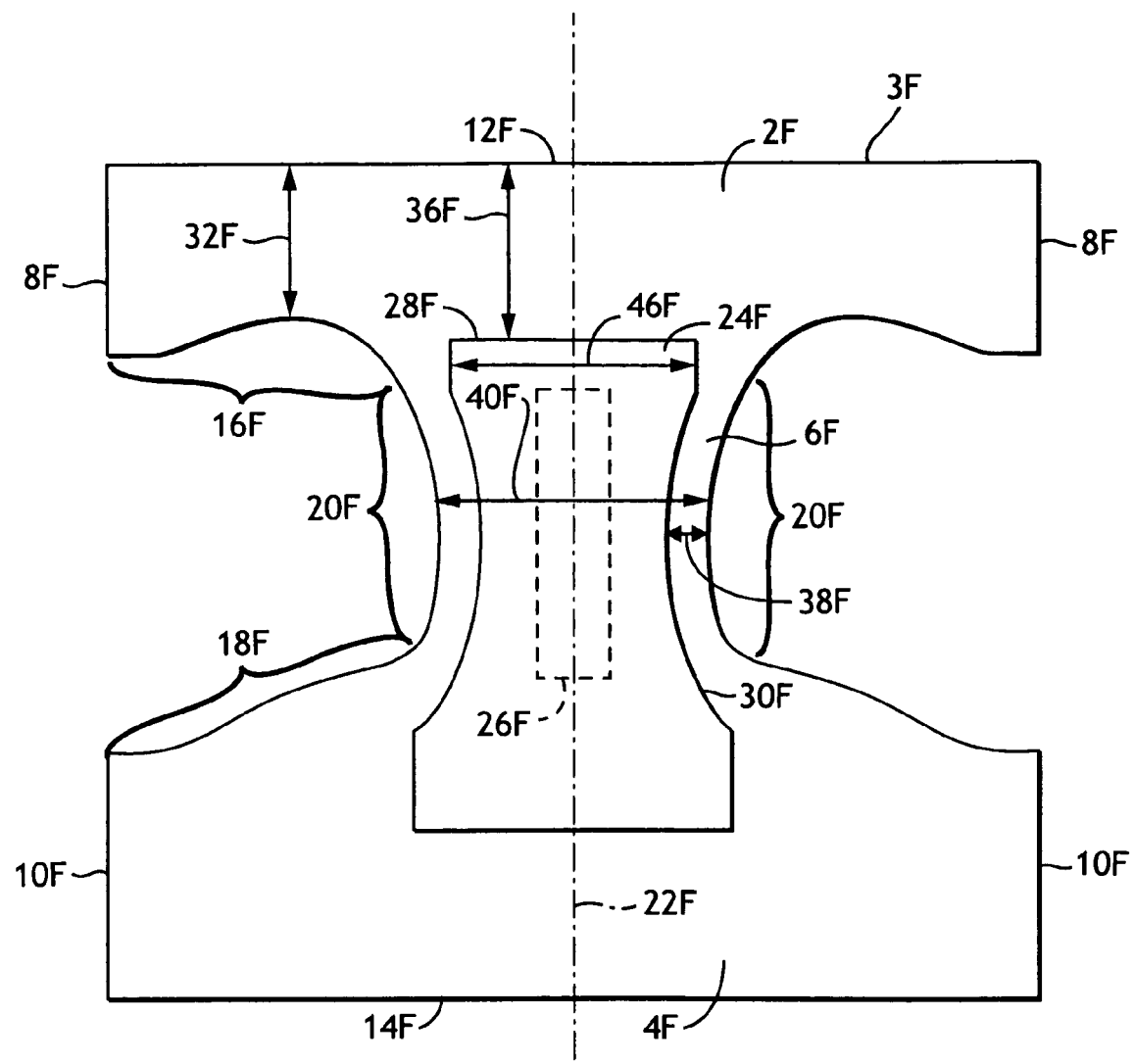
FIG. 2 depicts one representative example of a disposable adult-incontinence article adapted to be worn by a woman.

FIG. 2 depicts these same features, but for one representative example of a disposable, adult-incontinence article adapted for use by women. The same numbers used in FIG. 1 are used in FIG. 2, with the exception that the numbers in FIG. 2 are appended with the letter "F" to signify that these features correspond to those employed in an article adapted to be worn by women.

Table 1 below gives a comparison of two articles in an exemplary gender-specific array of articles. As noted above in the Summary section, it is not necessary that gender-specific articles in accordance with the present invention incorporate all of the features identified in Table 1. Nor does the invention encompass only those features listed in this table.

TABLE 1

| Feature | Article for Women | Article for Men |
| --- | --- | --- |
| Anterior Length | Shorter | Longer |
| Shape of Leg-Opening Front Edge | More convex toward waist-opening front edge | Less convex toward waist-opening front edge |
| Shape of Leg-Opening Back Edge | More concave toward waist-opening back edge | Less concave toward waist-opening back edge |
| Leg-Opening Perimeter | More | Less |
| Crotch Width | Narrower (Shorter) | Wider (Longer) |
| Waist/Absorbent Distance | Longer | Shorter |
| Frontal Area of Absorbent Core | Less | More |
| Frontal Transverse Span | Shorter | Longer |
| Graphic Disposed on Article | Different | Different |
| Gasket Width | Narrower (Shorter) | Wider (Longer) |

As noted elsewhere, one feature of particular embodiments of an array of gender-specific articles—comprising a disposable, adult-incontinence article adapted to be worn by a woman, and a disposable, adult-incontinence article adapted to be worn by a man—is that the article adapted to be worn by women has a shorter anterior length than the article adapted to be worn by men. This may be achieved, for example, when the leg-opening front edge of the women's article defines a boundary that is more convex toward the waist-opening front edge compared to the boundary defined by the leg-opening front edge of the man's article. It is believed that such convexity helps define a leg opening better suited to the shape of an average female user's thigh compared to the shape of an average male user's thigh. As noted elsewhere, as men age their legs tend to lose muscle mass, which results in thinner legs and a smaller circumference around the upper thigh. Surprisingly, the circumference of the legs of many male users of adult-incontinence products may actually be smaller than the circumference of the legs of many female users of adult-incontinence products. Also, a leg-opening front edge having a shorter anterior length is more likely to result in a boundary that better conforms to the curvature of the upper thigh of the typical female user of the article.

Another feature that may be employed in an array of gender-specific articles is a disposable, adult-incontinence article adapted to be worn by women that comprises a leg-opening back edge that defines a boundary that is more concave in a direction toward the waist-opening back edge compared to the boundary defined by the leg-opening back edge of a corresponding article adapted to be worn by men. A more concave boundary in the woman's article helps ensure coverage of the typical female user's buttocks.

Yet another characteristic that may be selected for use in an array of gender-specific articles is a disposable, adult-incontinence article adapted to be worn by women having a leg-opening perimeter that is greater than the leg-opening perimeter for the corresponding article adapted to be worn by men.

Because of differences in their respective physiologies, an array of gender-specific articles may include a disposable, adult-incontinence article adapted to be worn by women that has a smaller crotch width compared to the corresponding article for men.

The point at which urine exiting the body contacts a disposable absorbent article is different for men and women, given their physiological differences. Accordingly, the position of the absorbent in an article adapted to be worn by men may be shifted forward in the article, resulting in the distance between the waist-opening front edge and the front edge of the absorbent decreasing. This helps ensure that the point at which urine first contacts the article is on the absorbent core. A women's article will tend to employ the absorbent core at a position ensuring contact with a urination point that is not as far forward as that for a man.

The frontal area and/or frontal transverse span of the absorbent core may also be varied between an article adapted to be worn by men and an article adapted to be worn by women. Because a man's point of urination may move, the overall frontal area of the absorbent core in a disposable, adult-incontinence article adapted to be worn by men may be greater than the corresponding frontal area in a woman's article. Similarly, the frontal transverse span of the absorbent core in a disposable, adult-incontinence article adapted to be worn by men may be greater than the corresponding frontal transverse span of the absorbent core in a woman's article.

As discussed elsewhere, graphics may be disposed on an article adapted to be worn by women that are different than those disposed on an article adapted to be worn by men. In one example, one or more stripes of a desired width are disposed around the perimeter of the article in a location proximate to the waist-opening front edge, back edge, or both. The shape, color, number, or other characteristic of the stripes disposed on a man's article may be different from those disposed on the woman's article. For example, blue-colored stripes may be disposed around the perimeter of the waist region (i.e., that portion of the article proximate to the waist opening) of a man's article, while pink-colored stripes are disposed around the perimeter of the waist region of the corresponding woman's article. In another representative example, graphics may be disposed on the article so that the article more closely resembles the shape and look of woven underwear. So, for example, a graphic fly or opening may be employed on a man's article so that the article resembles men's woven underwear briefs.

Also, the distance between the edge of the absorbent core and the outermost elastic strand proximate to the nearest leg-opening side edge on a man's disposable adult-incontinence article may be greater than that in the corresponding article for a woman. Due to physiological differences between a man and a woman in the area of the crotch, this additional distance generally corresponds to there being additional substrate between the edge of the absorbent core and the outermost elastic member proximate to the side edge of the nearest leg opening. This substrate, which will typically be flexible and incorporate an elastic member proximate to the leg-opening side edge, acts, in a sense, as a gasket to help contain urine. As mentioned elsewhere, the circumference of an older man's leg tends to be smaller due to the loss of muscle mass, and often may be less than that of a woman. Accordingly, an increased gasket width helps to ensure the presence of sufficient material between the inner surface of a man's thigh and the absorbent core.

The preceding paragraphs outline various features that may be employed in an array of gender-specific, disposable, adult-incontinence articles, with these features differing in some way between an article adapted to be worn by a woman and an article adapted to be worn by a man. The article itself may employ many different components and subassemblies, so long as the array of gender-specific articles employs one or more of the novel features discussed elsewhere in this application. For example, the article may comprise an hour-glass-shaped liquid-impermeable substrate, such as a film, attached to an hour-glass-shaped liquid-permeable substrate, such as a nonwoven, with a cellulosic-fluff/superabsorbent-material absorbent core disposed between the liquid-impermeable and liquid-permeable substrate, which together define an absorbent assembly. Either of these substrates can be more complicated of course (e.g., laminates of nonwovens, films, or both; co-form materials; etc.), as can the absorbent core. Also, various pigments, odor-control agents, fillers, and other materials may be employed. Elastic materials such as strands or webs may be employed to help give the article elastomeric qualities in desired locations. For example, elastic members such as strands are often employed in the vicinity of the leg openings and waist to help ensure a close fit. Also, elastic members such as strands are often positioned below the waist-opening to effect a close fit around the lower torso of a user. For example, spaced-apart, substantially parallel elastic strands may be sandwiched between two nonwoven materials in the vicinity of the torso. Often the strands are attached to nonwoven facings, typically using adhesive, when the strands are in a stretched condition. The resulting laminate—elastic strands sandwiched between two nonwoven facings—is then allowed to retract, producing a gathered substrate capable of stretching and recovering its shape.

Note too that many different components and subassemblies may be used in disposable, adult-incontinence articles. For example, rather than the hourglass-shaped liquid-impermeable and liquid-permeable substrates described above, a single, hourglass-shaped liquid-permeable substrate may be formed (e.g., two polypropylene facings attached to one another, with elastic strand disposed between the facings in certain locations, such as proximate to the leg openings, waist opening, and those portions of the front and back of the article that will contact the lower torso of a user). To this liquid-permeable substrate or chassis 3 is attached an absorbent assembly 50, with the absorbent assembly comprising a cellulosic-fluff/superabsorbent absorbent core 24 sandwiched between a liquid-impermeable outer cover 54, such as a film, and a liquid-permeable liner 52, such as a nonwoven. Such a configuration is representatively illustrated in FIGS. 3-6. In particular embodiments, when the absorbent assembly 50 is attached to the hourglass-shaped, liquid-permeable chassis, the liquid-impermeable outer cover is attached to the chassis.

Other configurations are possible. For example, the article may be made by forming a front panel (or portion), a back panel (or portion), and attaching the two with a crotch portion comprising an absorbent assembly. And such articles may employ various fastening systems (including, e.g., refastenable systems such as those using hook-and-loop-type fasteners), separate waistbands attached to the article, side panels (e.g., elastomeric side panels), and many other such components or assemblies. It should be readily understood that the present invention encompasses many such configurations of disposable articles, so long as said articles employ one or more of the identified inventive features which are varied between an article adapted to be worn by women and an article adapted to be worn by men (whether in the form of a product array or an individual article). Similarly, many different methods, unit operations, and processes may be used when making gender-specific, disposable, adult-incontinence articles.

Figure 4:
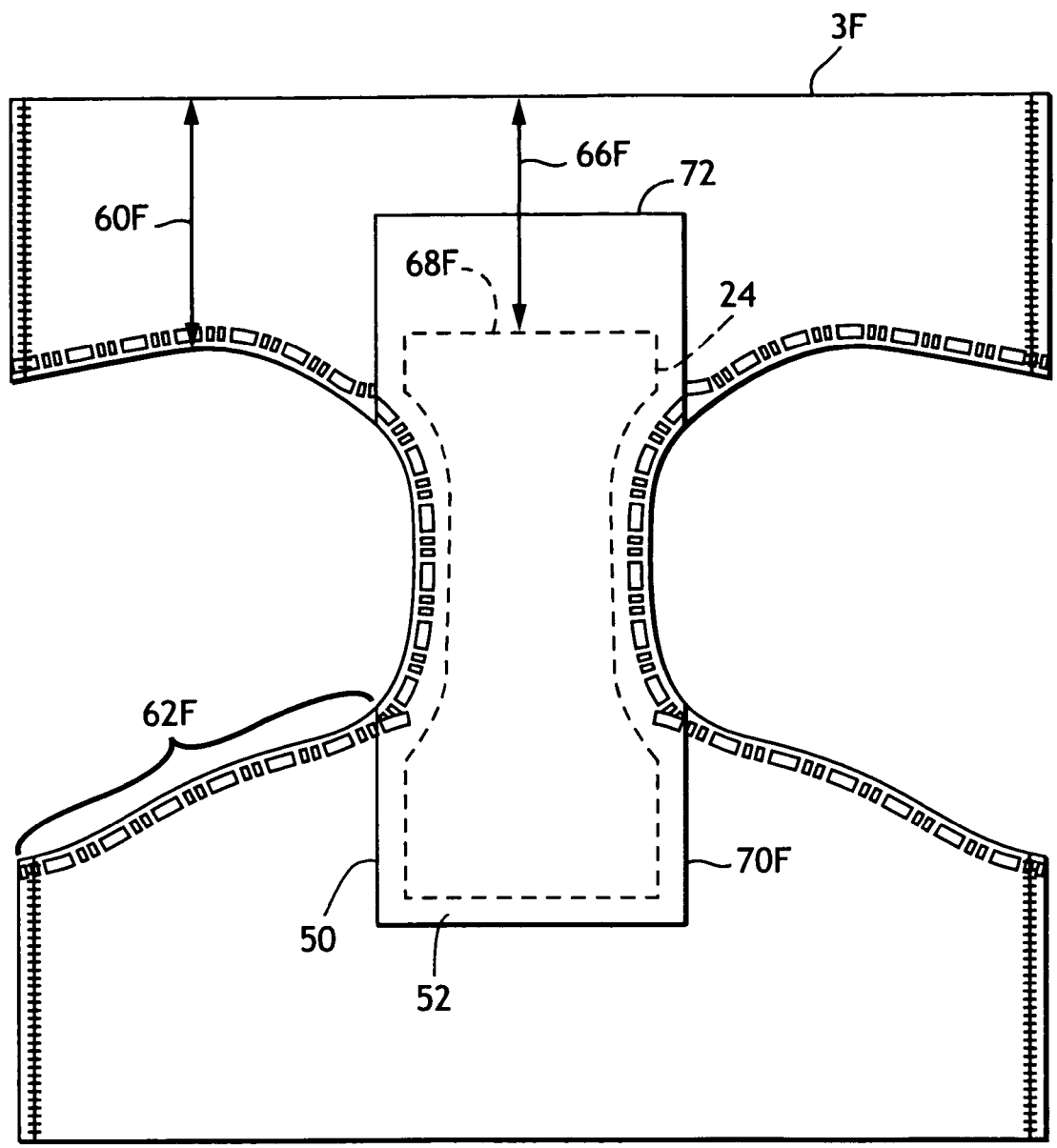
FIG. 4 depicts one representative example of a disposable adult-incontinence article adapted to be worn by a woman.
Figure 5:
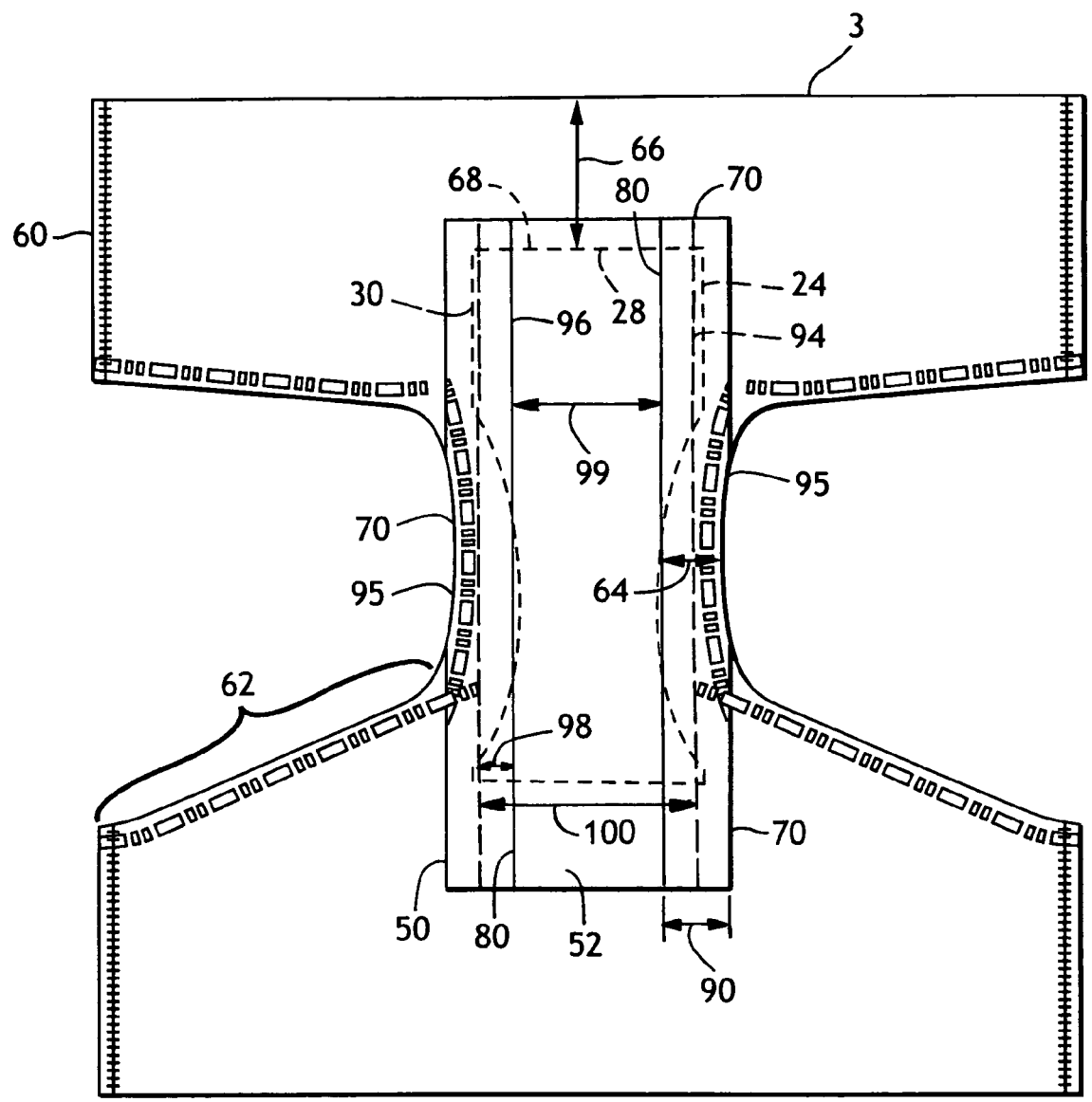
FIG. 5 depicts the article of FIG. 3 with containment flaps added.
Figure 6:
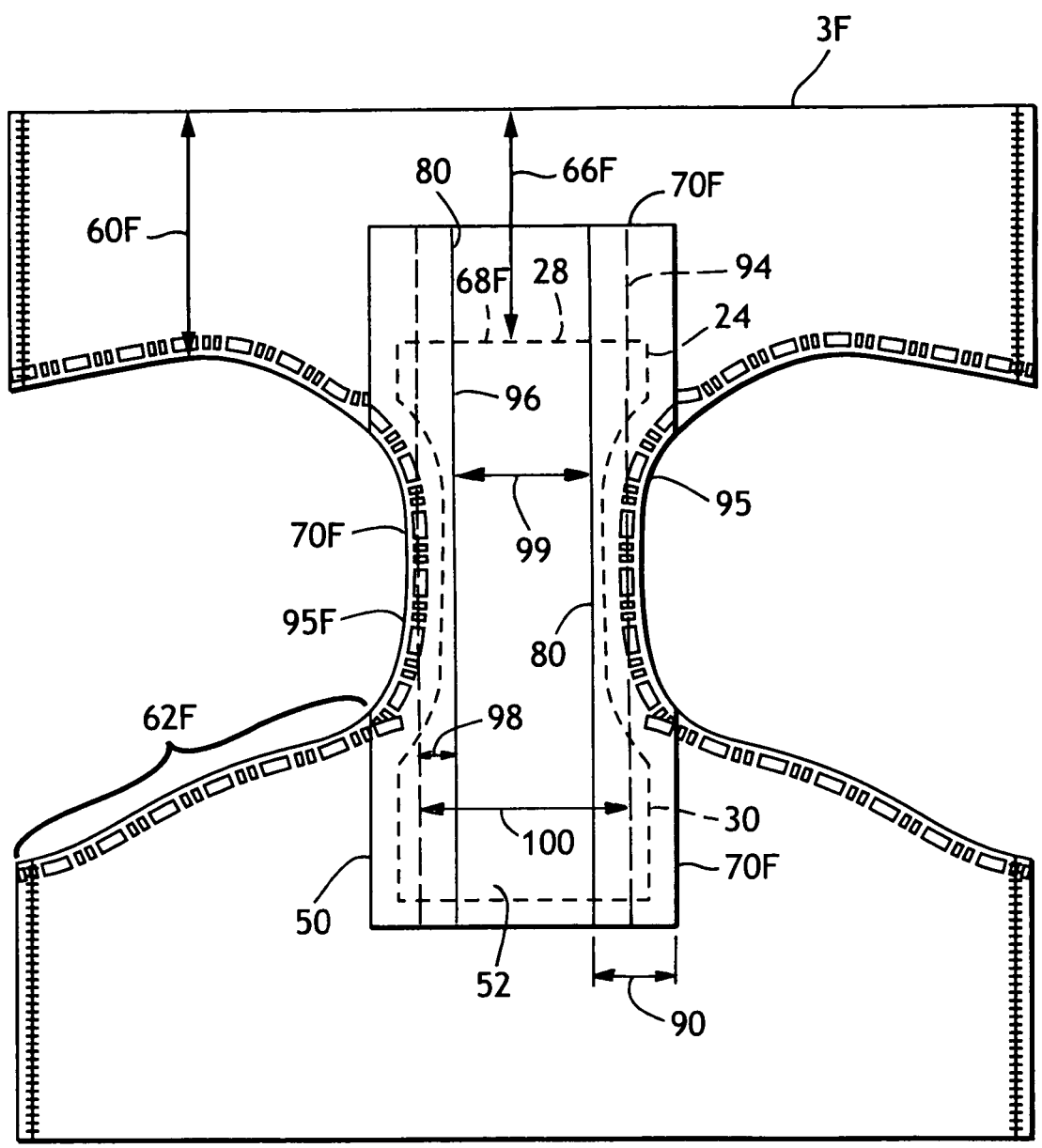
FIG. 6 depicts the article of FIG. 4 with containment flaps added.
Figure 7:
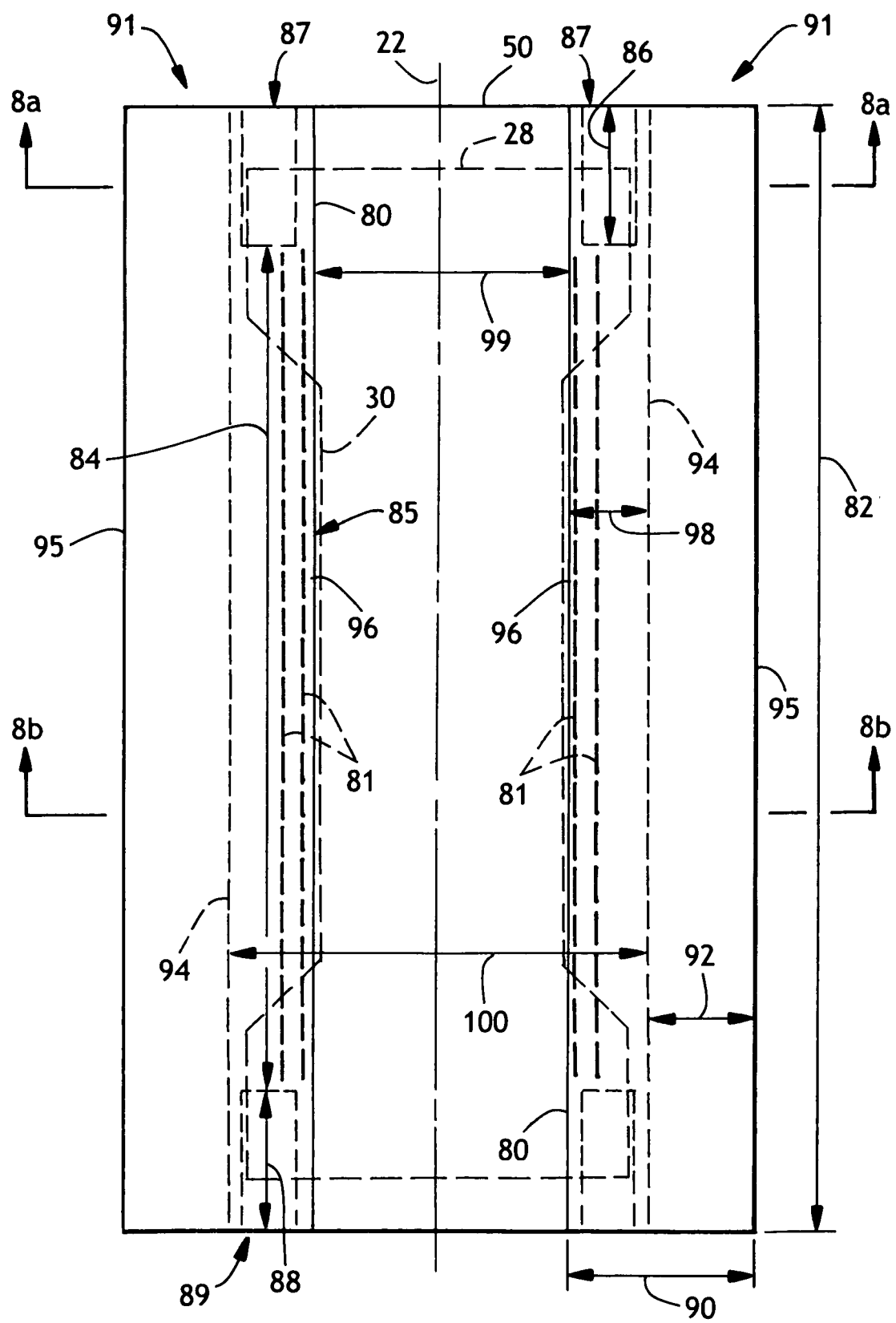
FIG. 7 depicts one representative example of an absorbent assembly having containment flaps.
Figure 8A:
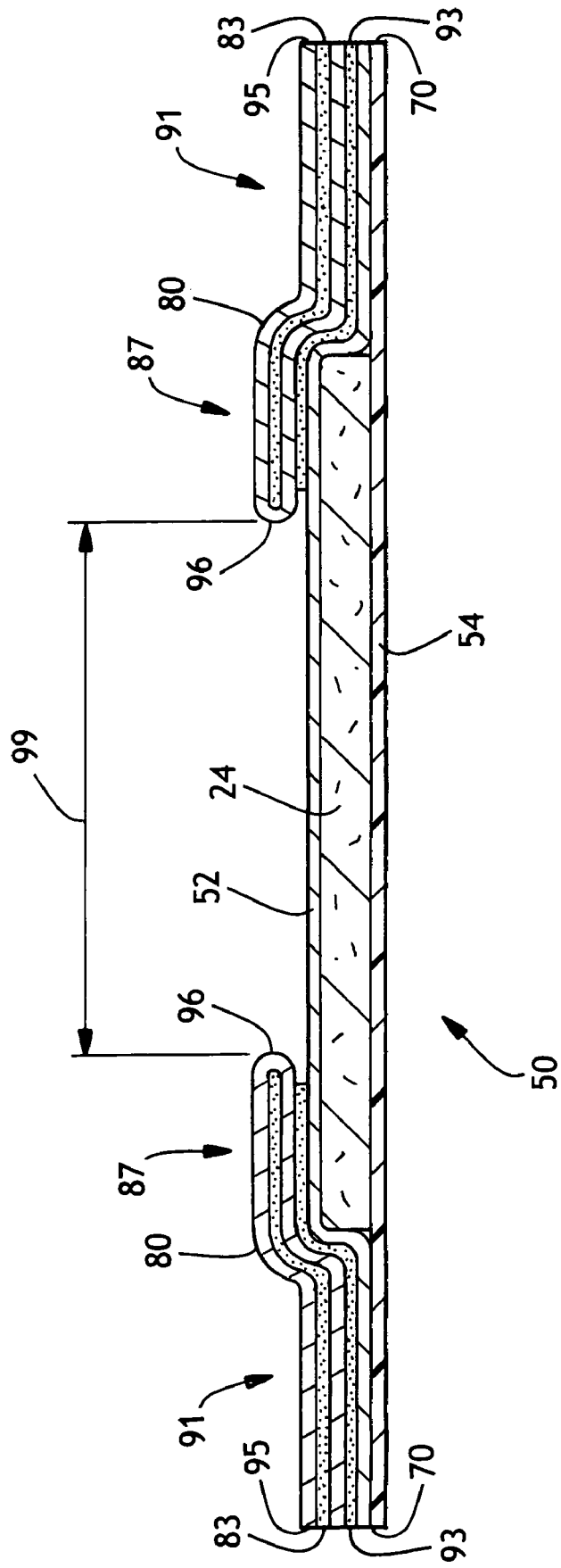
Figure 8B:
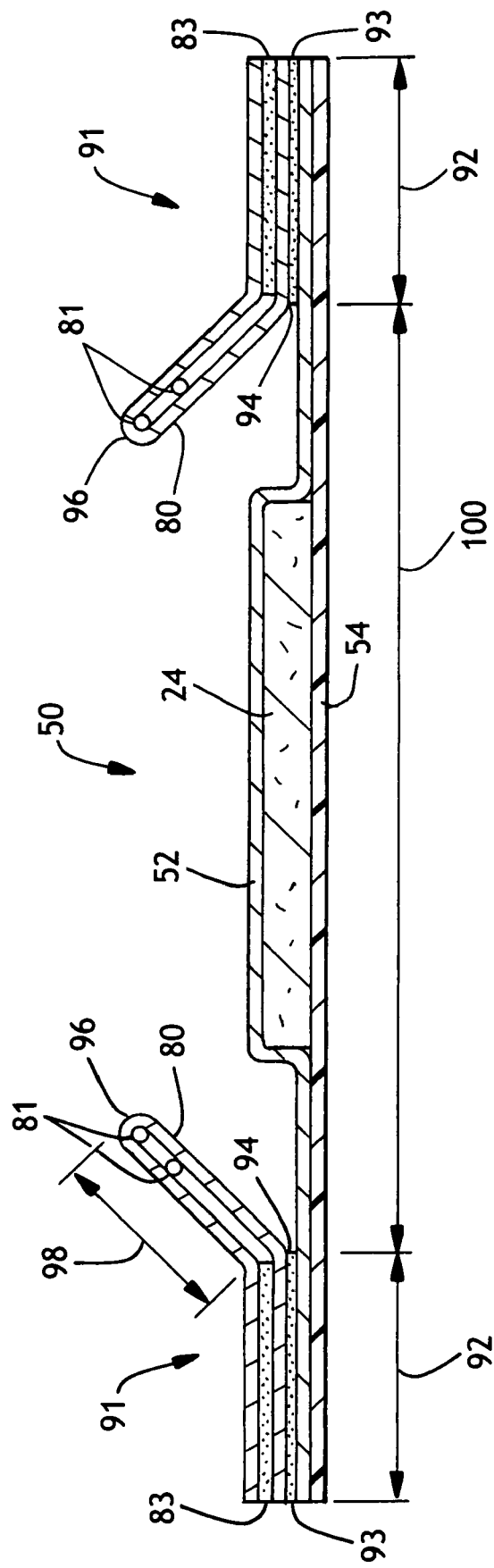
FIG. 8b is a cross-sectional view of the absorbent assembly of FIG. 7 taken along line 8b-8b.

A feature that is employed in particular embodiments of the gender-specific absorbent articles of the present invention is a pair of gender-specific containment flaps. The containment flaps are intended to reduce leakage of urine and/or feces out of the absorbent article. FIGS. 5 and 6 representatively illustrate a pair of containment flaps 80 disposed on an absorbent assembly 50, which is itself illustrated as being disposed on the chassis 3 of the article. FIGS. 5 and 6 are identical to FIGS. 3 and 4, except that containment flaps 80 have been added in FIGS. 5 and 6. FIG. 7 representatively illustrates an absorbent assembly 50 that has not been affixed to a garment chassis. FIG. 7 shows additional details of exemplary embodiments of the containment flaps used in conjunction with particular embodiments of the present invention, which shall now be discussed. (It is contemplated that the absorbent assembly 50 depicted in FIG. 7 could be added to an absorbent garment, such as being added to an adult incontinence garment chassis 3 as depicted in FIGS. 5 and 6.) FIGS. 8a and 8b depict cross-sectional views of the absorbent assembly of FIG. 7 taken along lines 8a-8a and 8b-8b, respectively.

The containment flaps can be formed of any of a variety of materials, including liquid-permeable or liquid-impermeable materials. For example, the containment flaps 80 can include a nonwoven material such as a spunbond, meltblown, spun laced or carded polymeric material, a film material such as a polyolefin or polyurethane film, a foam material or combinations thereof. The containment flaps 80 may also include materials described above as being suitable for the outer cover or bodyside liner. In a specific embodiment, the containment flaps 80 may be formed from a nonwoven material such as a spunbond or meltblown polyethylene or polypropylene material. Containment flap materials include nonwoven materials, such as thermoplastic polymers, such as polyolefins; bonded carded webs; film materials, such as ethylene vinyl acetate, and ethyl methacrylate films; foam materials, such as polyolefin foams; woven materials, such a woven polypropylene, polyethylene or polyester fabrics; and composites and laminates of the above nonwoven, film, foam, and woven materials.

Many nonwoven materials are formed from hydrophobic materials. Such hydrophobic materials result in nonwovens which are somewhat resistant to the flow of liquids. If it is desired that the containment flaps 80 be generally liquid pervious, such nonwoven materials may be treated with a surfactant to render them generally hydrophilic. Alternatively, if it is desired that the containment flaps 80 be liquid impervious, the containment flaps can include a liquid-impervious film such as a polyolefin film. In a specific embodiment, the containment flaps 80 comprise a spunbond/meltblown/spunbond laminate material having a basis weight of about 30 grams per square meter. In another embodiment, the flaps can comprise a hydrophobic polypropylene-based spunbond material.

Each containment flap 80 is characterized by a number of design variables. For example, in particular embodiments, each flap has a total length 82, an active length 84, a front end-zone tack-down length 86, a back end-zone tack-down length 88, an active portion longitudinal position, a folded width 90, an attached width 92, a proximal edge 94, a distal edge 96, a flap height 98, a flap tension, a distal-to-distal spacing 99, and a proximal-to-proximal spacing 100. (All flap dimensions are measured when the absorbent assembly 50 is in a laid-flat, fully extended configuration, with the exception of flap tension, whose measurement technique is described below.) Each flap 80 extends in a direction generally aligned with the longitudinal centerline 22 of the article. For example, each flap can be parallel, non-parallel, or partly parallel and partly non-parallel to the longitudinal centerline of the article. The total length 82 of the flap is the dimension of the flap as it extends in a direction generally aligned with the longitudinal centerline 22 of the article. The total length 82 of each flap can be equal to, shorter than, or longer than the length of the absorbent assembly 50. In particular embodiments, such as those depicted in FIGS. 5-7, the total length of each flap 80 is equal to the length of the absorbent assembly 50.

To provide each flap 80 with elasticization along at least a portion of its length 82, each flap 80 is provided with one or more elastic members 81. The elastic members are elongated, and operatively joined to the flap by being secured to the flap with adhesive (not shown) while in their elongated state. The flap substrate is then generally folded over onto itself to sandwich the one or more elastic members, as representatively illustrated in FIG. 8b. The sandwich may be sealed using any means known in the art, such as via the use of adhesive 83. In certain embodiments, the flap is folded entirely in half to form a "U-shaped" fold, as shown in FIGS. 8a and 8b. In other embodiments, the flap is folded only partially upon itself to form a "J-shaped" fold (not shown). Each folded flap defines a folded width 90.

In certain embodiments, such as those representatively illustrated in FIGS. 8a and 8b, the flap is constructed from a material that is not integral with either the bodyside liner or the garment-side outer cover. In other embodiments (not shown), the flap substrate is integral with the liner, the outer cover, or both. In embodiments in which the flap is not integral with either the liner or outer cover, but is instead formed of a distinct material, at least a portion of the total width of each flap is attached to the bodyside liner along at least a portion of the flap's length to define an attached portion 91 having an attached width 92. Such attachment can be accomplished by any suitable means known in the art, such as by the use of adhesive 93. The longitudinal edge of this attached portion 91 that is closest to the longitudinal centerline 22 is referred to as the flap proximal edge 94. The edge at which the remaining width of the flap terminates nearest the longitudinal centerline 22 of the article is referred to as the flap distal edge 96. The transverse distance between the proximal edge 94 and distal edge 96 on each flap 80 defines a flap height 98.

In the longitudinal central region of each flap, the portion of the flap between the proximal edge 94 and the distal edge 96 remains unadhered to the liner 52. In contrast, in the longitudinal end regions of each flap 80, the portion of the flap between the proximate edge 94 and the distal edge 96 is adhered to the liner 52 to define front end-zone tack-down regions 87 having front end-zone tack-down lengths 86, and back end-zone tack-down regions 89 having back end-zone tack-down lengths 88.

The elastic 81 is operatively joined in its elongated state to the flap 80 along at least a portion of the flap total length 82. In particular embodiments, the flap 80 is not elasticized in its end portions. For example, the elastic strands may be present in the end portions, but may be chopped or otherwise deadened to remove their elastic properties in this longitudinal region. In another example, adhesive is absent within the end portions of the flap within the flap fold, so that the elastic strands "snap back" from the end portions, leaving the end portion un-elasticized, a technique common in the art. The longitudinal portion of the flap in which the flap is operatively joined to the flap, thereby imparting elastic properties to the flap, defines a flap active portion 85 having a flap active length 84.

As shall be explained further below, the longitudinal position of the flap active portion 85 can vary depending to suit particular purposes. For example, the active portion 85 of the flap can be longitudinally centered in the article, or could be shifted to some degree toward the front or back waist-opening edges of the article. The longitudinal position of the flap active portion 85 can in particular embodiments be quantified by measuring the distance between the absorbent core front edge 28 and the end point of the flap active portion 85 closest to the absorbent core front edge 28. Alternatively, the longitudinal position of the flap active portion 85 can in particular embodiments be quantified by measuring the distance between the waist-opening front edge 12 of the product and the end point of the flap active portion 85 closet to the waist-opening front edge 12.

As shall also be explained further below, the spacing 99 between the distal edges 96 of a pair of flaps 80 in a disposable absorbent article ("distal-to-distal spacing") can vary to suit particular purposes. Such spacing can impact the leakage-reducing functions of the absorbent article. The distal-to-distal spacing 99 is measured when the article is in a laid-flat, fully extended configuration, and is the shortest transverse distance between the distal edges 96 of the flaps 80.

As shall also be explained further below, the spacing 100 between the proximal edges 94 of a pair of flaps 80 in a disposable absorbent article ("proximal-to-proximal spacing") can vary to suit particular purposes. Such spacing can impact the leakage-reducing functions of the absorbent article. The proximal-to-proximal spacing 100 is measured when the article is in a laid-flat, fully extended configuration, and is the shortest transverse distance between the proximal edges 94 of the flaps 80.

When the article is worn, the portion of a flap 80 that remains unadhered to the liner—i.e., the unattached portion—tends to assume an upright configuration (as representatively illustrated in FIG. 8*b*) by virtue of the elasticization in the active portion 85. In certain embodiments, such upright configuration can, as noted elsewhere, form a seal against the body, further assisting in minimize leakage during use.

Each flap 80 exhibits a flap tension in its active portion, due to the elasticization imparted by the elastic strands or members 81. The tension of containment flaps employed in articles in accordance with the present invention is determined by the following test method, which is otherwise referred to herein as an elastic tension test. Each absorbent assembly to be tested is hung from a conventional lightbox or other suitable device in an unfolded, vertical orientation with one end (e.g., the back end) of the absorbent assembly up and the bodyside liner of the absorbent assembly facing laterally outward away from the lightbox. (In some products, such as baby diapers, the absorbent assembly is generally the full length of the product. In other products, such as pull-on adult incontinence garments, the absorbent assembly is generally shorter than the full length of the product. In such cases, the absorbent assembly should first be removed from the larger absorbent chassis, such as by peeling away or cutting out the absorbent assembly from the garment chassis, taking care not to damage the containment flaps.) The lightbox includes a pair of fixed upper clamps spaced apart roughly in accordance with the approximate spacing between the containment flaps on the opposite sides of the absorbent assembly. The waistband, if any, at the back end of the absorbent assembly is generally fully stretched (e.g., to eliminate gathers in or otherwise straighten the waistband) and the clamps are clamped to the waistband without clamping any of the absorbent core therein. The operator then gently runs his or her fingers down the sides of the containment flaps to straighten and extend the absorbent assembly.

The waistband (if any) at the front (i.e., lower) end of the diaper is then generally fully stretched (i.e., to eliminate gathers in or otherwise straighten the waistband) and a clamp weight is secured to the waistband at the front end of the diaper so that the diaper hangs freely from the upper clamps in a longitudinally elongated configuration. The clamp weight is approximately 1,000 grams total mass and includes a pair of clamps spaced approximately 5.5 inches apart at their centerlines (e.g., spaced approximately the same as the clamps attached to the back end of the absorbent assembly) for attaching the clamp weight to the front end of the absorbent assembly.

With the absorbent assembly in this longitudinally elongated configuration, a pair of markings is made on each containment flap generally where the elastics are attached to the flap. More particularly, the markings on each containment flap are spaced longitudinally from each other a distance of about 178 mm and are equidistant from the longitudinal center of the active portion of the flap. The clamp weight is then removed from the absorbent assembly and the absorbent assembly is removed from the lightbox. Each containment flap is cut from the absorbent assembly by first cutting the containment flap inward from the free (i.e., distal) edge of the flap to the secured edge of the flap at longitudinally spaced locations which are approximately 0.5 inches (12.85 mm) beyond each of the markings (e.g., toward the nearest end of the absorbent assembly) made on the flap, and then cutting lengthwise generally adjacent the bead or strip of adhesive which secures the secured edge of the flap to the liner.

Each test specimen (e.g., the marked and cut portion of each containment flap) is then secured in a testing device by a generally fixed upper clip and a generally moveable lower clip, both of which are constructed to inhibit the specimen against slipping or becoming damaged upon tensioning the specimen. More particularly, the specimen is first secured at one end by the upper clip, with the specimen marking near the one end being aligned with the leading edge (e.g., the lowermost edge) of the upper clip so that the specimen hangs freely from the upper clip in a generally relaxed (e.g., unstretched) condition. The weight of the specimen is tared and then the other end of the specimen is secured by the lower clip, with the marking near this end of the specimen being aligned with the leading edge (e.g., uppermost edge) of the lower clip. The lower clip is then moved longitudinally away from the upper clip until the specimen is elongated longitudinally to about 90% of the previously achieved longitudinally elongated configuration (e.g., to a configuration in which the spacing between the markings on the specimen is about 160 mm, which is 90% of 178 mm) of the absorbent assembly. The specimen is maintained in this condition for about thirty seconds. The elastic tension is then measured and recorded using a suitable force gauge. The containment flaps (i.e., both right and left) of at least five like absorbent assemblies are tested using the identical procedure and the results are averaged to determine the elastic tension in the flaps.

The longitudinal edge 95 of the flap that is furthest from the longitudinal centerline 22 of the article can be positioned transversely inward of, positioned transversely outward of, or be transversely coterminous with the longitudinal edge 70 of the absorbent assembly 50. In certain embodiments, such as those representatively illustrated in FIGS. 5 and 6, a portion of the absorbent assembly has been cut out to provide shaping at the leg opening side edge 20. In the illustrated embodiments, the part of the attached portion 91 of each flap 80 has likewise been cut out to provide shaping, rending its longitudinal edges 95 coterminous with the side edges 70 of the absorbent assembly 50.

It has been discovered by the present inventors that, due to differences between males and females, certain containment flap design variables can be optimized to better suit users of a specific gender. Specifically, certain design variables can be configured in one way to best suit the performance requirements of the male user, but be configured in a different way to best suit the performance requirements of the female user. Such male/female differences in containment flap design variables apply to a variety of disposable absorbent articles, including training pants, enuresis pants, and adult incontinence articles. For ease of explanation, the following illustrative examples will address gender-specific containment flap design variables in the context of adult incontinence pull-on absorbent underwear.

In particular embodiments, the total length 82 of each containment flap 80 in a product adapted for males can be different that the total length 82 of each containment flap 80 in a product adapted for females. For example, the total length 82 of each containment flap 80 in a product adapted for males can be longer than or shorter than the total length 82 of each containment flap 80 in a product adapted for females. In particular embodiments, the total length of each containment flap in a product adapted for males is at least ten percent longer than, or ten percent shorter than, each containment flap in a corresponding product adapted for females.

In particular embodiments, the active length 84 of each containment flap 80 in a product adapted for males can be different that the active length 84 of each containment flap 80 in a product adapted for females. For example, the active length 84 of each containment flap 80 in a product adapted for males can be longer than or shorter than the active length 84 of each containment flap 80 in a product adapted for females. In one preferred embodiment, the active length 84 of each containment flap 80 in a product adapted for males is longer than the active 84 length of each containment flap 80 in a product adapted for females. For example, in particular embodiments, the active length of each containment flap in an adult incontinence garment adapted for males is from about 270 millimeters to about 310 millimeters, and more particularly from about 285 millimeters to about 300 millimeters, while the active length of each containment flap in a corresponding adult incontinence garment adapted for females is from about 170 millimeters to about 290 millimeters, and more particularly from about 250 millimeters to about 280 millimeters.

In particular embodiments, the front end-zone tack down length 86 of each containment flap 80 in a product adapted for males can be different that the front end-zone tack-down 86 length of each containment flap 80 in a product adapted for females. For example, the front end-zone tack-down length 86 of each containment flap 80 in a product adapted for males can be longer than or shorter than the front end-zone tack-down 86 length of each containment flap in a product adapted for females. In one preferred embodiment, the front end-zone tack down 86 length of each containment flap 80 in a product adapted for males is shorter than the front end-zone tack-down length 86 of each containment flap 80 in a product adapted for females.

In particular embodiments, the back end-zone tack down length 88 of each containment flap 80 in a product adapted for males can be different that the back end-zone tack-down length 88 of each containment flap 80 in a product adapted for females. For example, the back end-zone tack-down length 88 of each containment flap 80 in a product adapted for males can be longer than or shorter than the back end-zone tack-down length 88 of each containment flap 80 in a product adapted for females. In one preferred embodiment, the back end-zone tack down length 88 of each containment flap 80 in a product adapted for males is longer than the back end-zone tack-down length 88 of each containment flap 80 in a product adapted for females.

In particular embodiments, the active-portion longitudinal position of each containment flap 80 in a product adapted for males can be different that the active-portion longitudinal position of each containment flap 80 in a product adapted for females. For example, the active-portion longitudinal position of each containment flap 80 in a product adapted for males can be longer than or shorter than the active-portion longitudinal position of each containment flap 80 in a product adapted for females. In one preferred embodiment, the active-portion longitudinal position of each containment flap 80 in a product adapted for males is closer to the front of the product than the active-portion longitudinal position of each containment flap 80 in a product adapted for females. For example, in particular embodiments, the active-portion longitudinal position of each containment flap in an adult incontinence garment adapted for males begins about 100 millimeters to about 150 millimeters, and more particularly from about 110 millimeters to about 140 millimeters, from the waist-opening front edge of the product, while the active-portion longitudinal position of each containment flap in a corresponding adult incontinence garment adapted for females is from about 190 millimeters to about 260 millimeters, and more particularly from about 200 millimeters to about 230 millimeters, from the waist-opening front edge of the product.

In particular embodiments, the height 98 of each containment flap 80 in a product adapted for males can be different that the height 98 of each containment flap 80 in a product adapted for females. For example, the height 98 of each containment flap 80 in a product adapted for males can be greater than or less than the height 98 of each containment flap 80 in a product adapted for females. In one preferred embodiment, the height 98 of each containment flap 80 in a product adapted for males is greater than the height 98 of each containment flap 80 in a product adapted for females. For example, in particular embodiments, the height of each containment flap in an adult incontinence garment adapted for males is from about 1 inch (25 millimeters) to about 1.25 inches (32 millimeters), while the height of each containment flap in a corresponding adult incontinence garment adapted for females is from about 0.75 inch (19 millimeters) to about 1 inch (25 millimeters).

In particular embodiments, the tension of each containment flap 80 in a product adapted for males can be different that the tension of each containment flap 80 in a product adapted for females. For example, the tension of each containment flap 80 in a product adapted for males can be greater than or less than the tension of each containment flap 80 in a product adapted for females. In one desirable embodiment, the tension of each containment flap 80 in a product adapted for males is less than the tension of each containment flap 80 in a product adapted for females. For example, in particular embodiments, the tension of each containment flap in an adult incontinence garment adapted for males is less than 50 grams, while the tension of each containment flap in a corresponding adult incontinence garment adapted for females is equal to or greater than 50 grams. In other embodiments, the tension of each containment flap in an adult incontinence garment adapted for females is less than 50 grams, while the tension of each containment flap in a corresponding adult incontinence garment adapted for males is equal to or greater than 50 grams.

In particular embodiments, the distal-to-distal spacing 99 between the flaps 80 in a product adapted for males can be different that the distal-to-distal spacing 99 between the flaps 80 in a product adapted for females. For example, the distal-to-distal spacing 99 in a product adapted for males can be greater than or less than the distal-to-distal spacing 99 in a product adapted for females. In one preferred embodiment, the distal-to-distal spacing 99 in a product adapted for males is greater than the distal-to-distal spacing 99 in a product adapted for females. For example, in particular embodiments, the distal-to-distal spacing in an adult incontinence garment adapted for males is at least 100 millimeters, while the distal-to-distal spacing in a corresponding adult incontinence garment adapted for females is less than 100 millimeters.

In particular embodiments, the proximal-to-proximal spacing 100 between the flaps 80 in a product adapted for males can be different that the proximal-to-proximal spacing 100 between the flaps 80 in a product adapted for females. For example, the proximal-to-proximal spacing 100 in a product adapted for males can be greater than or less than the proximal-to-proximal spacing 100 in a product adapted for females. In one preferred embodiment, the proximal-to-proximal spacing 100 in a product adapted for males is greater than the proximal-to-proximal spacing 100 in a product adapted for females. For example, in particular embodiments, the proximal-to-proximal spacing in an adult incontinence garment adapted for males is at least 150 millimeters, while the proximal-to-proximal spacing in a corresponding adult incontinence garment adapted for females is less than 150 millimeters.

It should be noted that when gender specific constructions for various features (such as containment flaps) are discussed herein, it is contemplated that, when a comparison is made between products having one or more design variables specifically tailored to males on the one hand and females on the other hand, the male and female products having those gender specific features are designed for wearers of generally the same size. For example, if an adult incontinence garment is offered in three sizes for males (such as small, medium, and large), as well as three different sizes for females (such as small, medium and large), for a total of six different product codes, a comparison of any gender-specific design variable (e.g., containment flap height) should be examined for similarly sized products (e.g., compare male small to female small, male medium to female medium, and male large to female large). Likewise, if an adult incontinence garment is offered in varying absorbencies—such as low and high— each for both genders, a comparison of any gender-specific design variable (e.g., containment flap height) should be examined for products of similar absorbency (e.g., compare male low absorbency to female low absorbency, and male high absorbency to female high absorbency) for a particular size.

It should also be noted that the gender-specific containment flap features discussed above could constitute the only gender-specific feature in an offering of gender-specific absorbent articles, or, alternatively, could be used in concert with other gender-specific garment design features, such as those discussed above. For example, the design differences between an adult incontinence garment adapted for males and an adult incontinence garment adapted for females could be limited to one or more design differences directed to containment flap features. Alternatively, the design differences between an adult incontinence garment adapted for males and an adult incontinence garment adapted for females could include design differences directed to containment flap features as well as design differences directed to other features, such as, for example, leg cut-out shape, gasket width, crotch width, etc.

The articles themselves are typically stored, shipped, and sold in packages, such as bags made of polymeric film Another representative version of the invention is an array of disposable adult-incontinence articles comprising one or more of the inventive dimensional (e.g., those inventive features directed to a length, width, distance, or other such measurement), ornamental (e.g., those inventive features directed to disposing a graphic on an article) or other gender-specific features discussed above, with the first disposable adult-incontinence article contained in a first package (e.g., a container such as a bag) having a first statement or first indicia disposed thereon, wherein the first article is adapted to be worn by women; and a second disposable adult-incontinence article contained in a second package (e.g., a container such as a bag) having a second statement or second indicia disposed thereon, wherein the second article is adapted to be worn by men; wherein the first statement or indicia associates the article with use by women and the second statement or indicia associates the article with use by men. The packages may also have different graphics, colors, symbols, logos, or other such representations, depending on whether the articles contained therein are adapted to be worn by men or women. Furthermore, for those gender-specific articles not part of an array, these same embodiments employing packages may be used for a single, gender-specific article.

For example, a package—which generally will be in the form of a container such as a plastic bag—containing disposable, adult-incontinence articles adapted to be worn by men may have: a picture of a man; text associating the article with use by a man; size and/or absorbency information specific to men; a graphic representation of the articles contained therein that, by virtue of the different graphics disposed on the articles themselves, are different—e.g., a graphic representation of an article adapted to be worn by men having one or more blue stripes proximate to the waist opening; text communicating to a user one or more features making the article gender-specific; or some combination thereof.

Similarly, in another exemplary version, a package containing disposable, adult-incontinence articles adapted to be worn by women may have: a picture of a woman; text associating the article with use by a woman; size and/or absorbency information specific to women; a graphic representation of the articles contained therein that, by virtue of the different graphics disposed on the articles themselves, are different—e.g., a graphic representation of an article adapted to be worn by women having one or more pink stripes proximate to the waist opening; text communicating to a user one or more features making the article gender-specific; or some combination thereof.

A manufacturer, seller, or distributor of the inventive array of gender-specific articles may seek to create awareness of said articles so that users enjoy the benefits of said gender-specific articles. Accordingly, another representative version of the invention is a method of providing a gender-specific, disposable, adult-incontinence article, the method comprising the steps of transmitting a statement embodied in a tangible medium that refers to the gender-specific, disposable, adult-incontinence article; and positioning in the hands of a user a disposable, adult-incontinence article adapted for the gender of the user.

A statement may be transmitted using a variety of communications, statements, messages, or copy; which could take the form of (i.e., be embodied in a medium such as) a newspaper advertisement, a television advertisement, a radio or other audio advertisement, items mailed directly to addressees, items emailed to addressees, Internet Web pages or other such postings, free standing inserts, coupons, various promotions (e.g., trade promotions), co-promotions with other companies, boxes or packages containing the product, and other such forms of disseminating information to consumers or potential consumers.

As noted above, some versions of the present invention may not contain an article adapted for use by men and an article adapted for use by women. Instead, some versions of the invention comprise a unisex, disposable, adult-incontinence article and: (1) a disposable-adult incontinence article adapted to be worn by women comprising one or more of the inventive features described herein; or (2) a disposable-adult incontinence article adapted to be worn by men comprising one or more of the inventive features described herein. Various packaging and marketing techniques, including those described above, may be employed in conjunction with the aforementioned arrays comprising a unisex article.

Also, as noted above, certain embodiments of the present invention encompass gender-specific, disposable, adult-incontinence articles comprising one or more fit features, leg-opening features, and/or containment flap features. As with the aforementioned arrays, applicable packaging and marketing techniques, including those described above, may be employed in conjunction with these gender-specific articles. So, for example, in some versions of the invention, a disposable, adult-incontinence article adapted for women that comprises a fit feature, leg-opening feature, or containment flap feature is contained in a container, and a statement or indicia disposed on the container associates the fit feature, leg-opening feature, or containment flap feature with use of the article by women. In other versions of the invention, a disposable, adult-incontinence article adapted for men that comprises a fit feature, leg-opening feature, or containment flap feature is contained in a container, and a statement or indicia disposed on said container associates the fit feature, leg-opening feature, or containment flap feature with use of the article by men.

EXAMPLES

The following example representatively illustrates certain features that can be used in conjunction with the present invention. An array of gender-specific, disposable adult-incontinence articles was made. The articles were made using conventional materials and processes, and generally corresponded to the shapes depicted in FIGS. 1 and 2. More detailed drawings generally corresponding to those articles that were made are presented in FIG. 3 (male article) and 4 (female article).

The materials employed included polypropylene nonwoven materials for much of the chassis construction; film as the moisture barrier/backsheet/outer cover for the absorbent assembly; an absorbent core comprising cellulosic fluff and superabsorbent material; and elastic strands around the waist opening, leg opening, and portions of the front and back panels/portions of the article. Hot-melt adhesive or ultrasonic energy was used to attach the components to one another. In this exemplary embodiment, a polypropylene nonwoven material having an hourglass-like shape served as the outer cover. To this were attached nonwoven front and back panels at the front and back portions of the article (with elastic strand sandwiched at various locations between these nonwoven front and back panels and the nonwoven outer cover). The front panel extended longitudinally from a location proximate to the waist-opening front edge to a location proximate to the crotch portion (but did not substantially overlay the crotch portion of the hourglass-like outer cover). The back panel extended longitudinally from a location proximate to the waist-opening back edge to a location proximate to the crotch portion (but, like the front panel, did not substantially overlay the crotch portion of the hourglass-like polypropylene outercover). Both the front panel and the back panel extended transversely from a location proximate to one side edge to the opposing side edge of the front portion and the back portion of the article.

An absorbent insert comprising a fluff/superabsorbent core sandwiched between a barrier/backsheet material (a film) and a body-side liner (a nonwoven material) was attached to the aforementioned assembly of an hourglass-like shaped outer cover having elastic strand sandwiched between front and back nonwoven panels at the front portion and the back portion of the article. Approximate dimensions and inter-relationships between the two articles are given in Table 2.

Figure 3:
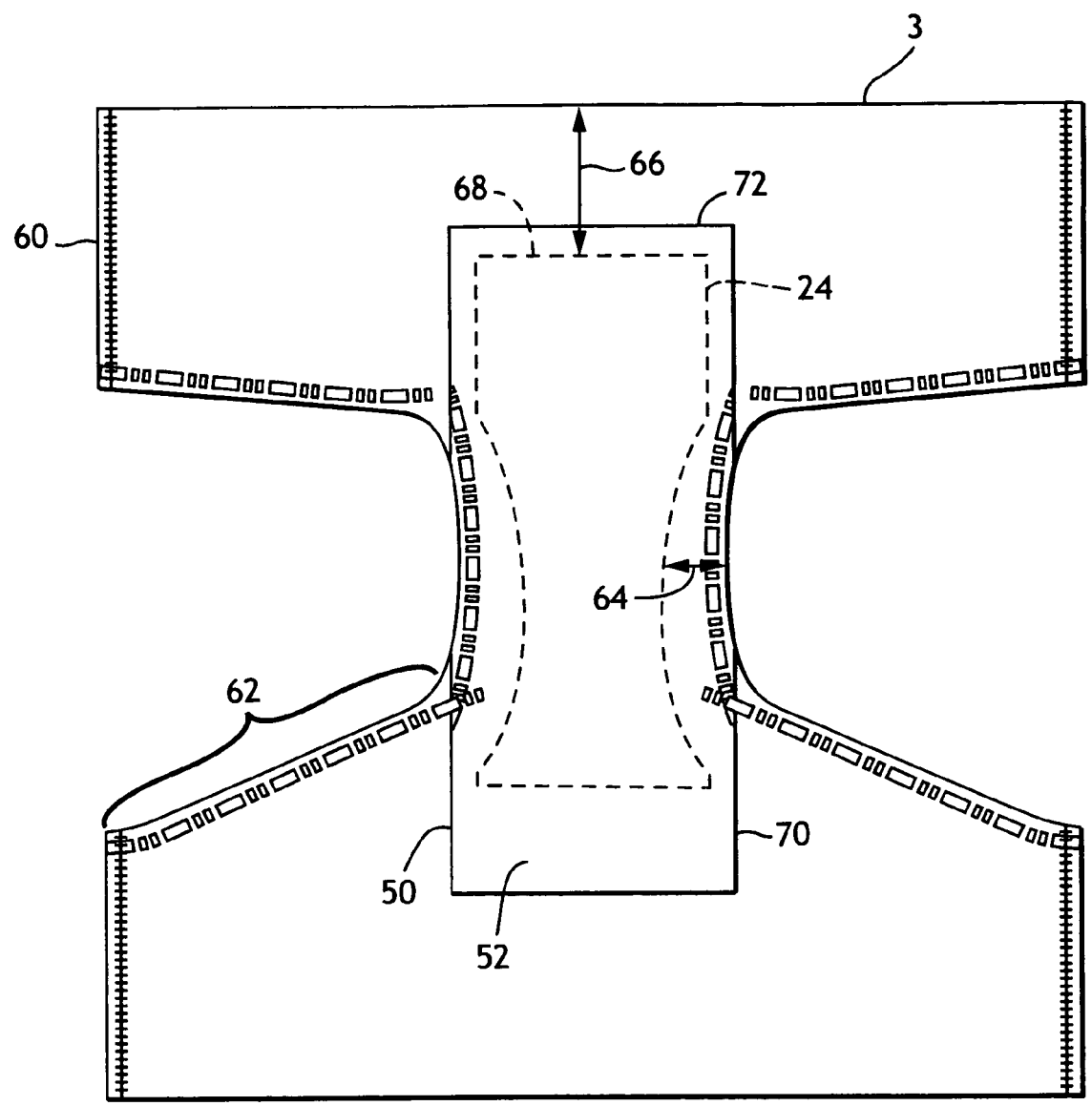
FIG. 3 depicts one representative example of a disposable adult-incontinence article adapted to be worn by a man.

The anterior length 60 for the men's article was about 210 millimeters, and overlaid the side edge of the front portion, given that the leg-opening front edges were generally linear, and proceeded upward at a slight angle from a location proximate to the crotch portion to the side edge itself (see FIG. 3). The anterior length 60F for the women's article was about 190 millimeters, however, and was measured from the point on the leg-opening front edge closest to the waist-opening front edge (see FIG. 4). This line, which is parallel to the longitudinal centerline of the article, is inward of the side edge of the front portion, given that the curvilinear boundary established by the leg-opening front edge of the women's article is more convex in a direction toward the waist opening front edge, compared to the corresponding, linear boundary established by the leg-opening front edge of the corresponding men's article. The leg-opening front edge of the women's article, having greater convexity, is better adapted to conform to the curved surface of the upper thigh region of a typical female user of such disposable, adult-incontinence articles.

An examination of FIG. 3 shows that the leg-opening back edges 62 of this exemplary version of an article adapted to be worn by men was also substantially linear, and proceeded downward at some angle from a location proximate to the crotch portion to the side edge of the back portion. The leg-opening back edge 62F of the exemplary women's article, however, does not define a substantially linear boundary, and instead defines a curvilinear boundary that is more concave in a direction toward the waist-opening back edge. The leg-opening back edge of the women's article, having greater concavity, is better adapted to ensure coverage of the buttocks region of a typical female user of such disposable, adult-incontinence articles.

Table 2 also shows that the perimeter of the leg-opening (which equates to the sum of the lengths of the leg-opening back, side, and front edges) for the women's article is greater than the perimeter of the leg-opening of the men's article.

Again, this leg-opening feature is consistent with the observation that men, as they age, tend to lose muscle mass in their legs, resulting in many male adult-incontinence-product users typically having a smaller thigh circumference than many female adult-incontinence-product users.

Furthermore, Table 2 shows that the man's article has a crotch width and a gasket width greater than the crotch width and gasket width of the corresponding women's article. The gasket width 64 (see FIG. 3) of the men's article was about 40 millimeters and the gasket width of the women's article was about 20 millimeters (not shown on FIG. 4 due to the close proximity of the edge of the absorbent core to the outermost elastic member nearest the leg-opening side edge, but measured at the same location as the corresponding location on the men's article: along a line in a transverse direction intersecting the center of the leg-opening side edge).

Also, the location of the absorbent was shifted forward for the men's article, compared to the women's article, to accommodate the point at which urine typically exits a man's body compared to a woman's body. Accordingly, the waist/absorbent distance 66 for the men's article was about 120 millimeters, and the waist/absorbent distance for the corresponding women's article 66F was about 180 millimeters. It should be noted that these distances were determined from the edge of the absorbent core (68 and 68F, respectively, in FIGS. 3 and 4). The edges 70 and 70F correspond to the side edges of the substrates encasing the absorbent core (i.e., the side edges of the absorbent assembly), and the edges 72 and 72F correspond to the end edges of the substrates encasing the absorbent core (i.e., the end edges of the absorbent assembly), and these substrates extend beyond the absorbent core itself to create a flexible flange surrounding the core. As discussed above, gasket width and waist/absorbent length/distance is measured from the edge of the absorbent core, not the edge of any substrate encasing and extending substantially beyond the edge of the absorbent core. It should also be noted that FIGS. 1 and 2 show the absorbent core, and a surge material, but not the outer perimeter of any substrate encasing the absorbent core and surge material. FIGS. 3 and 4, on the other hand, do not show a surge material, but do show both the absorbent core and the perimeter of the substrates used to encase the absorbent core.

Finally, while not shown, different colored stripes were disposed around each article at a location proximate to the waist opening. In this representative embodiment, a plurality of blue stripes were disposed around the perimeter of the men's article, and a plurality of pink stripes were disposed around the perimeter of the women's article.

TABLE 2

| Feature | Article for Women | Article for Men |
|---|---|---|
| Anterior Length | 190 mm | 210 mm |
| Shape of Leg-Opening Front Edge | More convex toward waist-opening front edge | Less convex toward waist-opening front edge |
| Shape of Leg-Opening Back Edge | More concave toward waist-opening back edge | Less concave toward waist-opening back edge |
| Leg-Opening Perimeter | 785 mm | 740 mm |
| Crotch Width | 155 mm | 195 mm |
| Waist/Absorbent Distance | 180 mm | 120 mm |
| Frontal Area of Absorbent Core | Less | More |
| Graphic Disposed on Article | Pink-colored stripes proximate to waist opening | Blue-colored stripes proximate to waist opening |
| Gasket Width | 20 mm | 40 mm |

FIGS. 5 and 6 illustrate exemplary gender-specific absorbent articles similar to those depicted in FIGS. 3 and 4, but with containment flaps added. Although the absorbent articles depicted in FIGS. 5 and 6 differ in the features listed in Table 2, such differences are optional; the products could, if desired, differ only in one or more gender-specific containment-flap features as outlined above. One representative example of specific values for certain of the containment flap features that could vary in an array of absorbent articles having gender-specific flap features appears in Table 3.

TABLE 3

| Feature | Article for Women | Article for Men |
|---|---|---|
| Flap active length | 270 mm | 300 mm |
| Active portion longitudinal position (distance from front waist edge) | 222 mm | 131 mm |
| Distal-to-distal spacing | 81 mm | 121 mm |
| Flap height | 19 mm | 25 mm |

What is claimed is:

1. An array of gender-specific disposable absorbent articles, the array comprising:
   a first disposable absorbent article adapted to be worn by males, the article comprising:
      a chassis comprising a garment-side outer cover, a bodyside liner, and an absorbent core sandwiched between the outer cover and liner, the chassis defining a waist opening front edge, a waist opening back edge, two side edges connecting the waist opening front and back edges, the absorbent core defining an absorbent front edge and an absorbent back edge; and
      a first pair of containment flaps disposed on the chassis, each flap defining a proximal end and a distal end and each flap having a first flap active length, a first flap active portion longitudinal position, a first flap tension, and a first flap height, each pair of flaps defining a first distal-to-distal spacing and a first proximal-to-proximal spacing; and
   a second disposable absorbent article adapted to be worn by females, the article comprising:
      a chassis comprising a garment-side outer cover, a bodyside liner, and an absorbent core sandwiched between the outer cover and liner, the chassis defining a waist opening front edge, a waist opening back edge, two side edges connecting the waist opening front and back edges, the absorbent core defining an absorbent front edge and an absorbent back edge; and
      a second pair of containment flaps disposed on the chassis, each flap defining a proximal end and a distal end and each flap having a second flap active length, a second flap active portion longitudinal position, a second flap tension, and a second flap height, each pair of flaps defining a second distal-to-distal spacing and a second proximal-to-proximal spacing,
   wherein the first pair of containment flaps differs from the second pair of containment flaps in at least one structural feature, said structural feature being flap active portion longitudinal position, the first flap active portion longitudinal position being further forward than the second flap active portion longitudinal position.

2. The array of gender-specific absorbent articles of claim 1 wherein the articles are pant-like adult incontinence articles.

3. The array of gender-specific absorbent articles of claim 1, wherein the first pair of containment flaps differs from the second pair of containment flaps in at least two structural features.

4. The array of gender-specific absorbent articles of claim 1 wherein the first article is contained in a first package and the second article is a contained in a second package, wherein the first package includes indicia which denotes that the first article is adapted for use by males, and the second package includes indicia which denotes that the second article is adapted for use by females.

5. The array of gender-specific absorbent articles of claim 4, wherein the indicia on the first package denotes that the first article is uniquely adapted to address protection issues for males, and the indicia on the second package denotes that the second article is uniquely adapted to address protection issues for females.

6. A method of marketing gender-specific absorbent articles, comprising:
  providing a first disposable absorbent article adapted to be worn by males, the article comprising:
    a chassis comprising a garment-side outer cover, a bodyside liner, and an absorbent core sandwiched between the outer cover and liner, the chassis defining a waist opening front edge, a waist opening back edge, two side edges connecting the waist opening front and back edges, the absorbent core defining an absorbent front edge and an absorbent back edge; and
    a first pair of containment flaps disposed on the chassis, each flap defining a proximal end and a distal end and each flap having a first flap active length, a first flap active portion longitudinal position, a first flap tension, and a first flap height, each pair of flaps defining a first distal-to-distal spacing and a first proximal-to-proximal spacing; and
  providing a second disposable absorbent article adapted to be worn by females, the article comprising:
    a chassis comprising a garment-side outer cover, a bodyside liner, and an absorbent core sandwiched between the outer cover and liner, the chassis defining a waist opening front edge, a waist opening back edge, two side edges connecting the waist opening front and back edges, the absorbent core defining an absorbent front edge and an absorbent back edge; and
    a second pair of containment flaps disposed on the chassis, each flap defining a proximal end and a distal end and each flap having a second flap active length, a second flap active portion longitudinal position, a second flap tension, and a second flap height, each pair of flaps defining a second distal-to-distal spacing and a second proximal-to-proximal spacing,
  wherein the first pair of containment flaps differs from the second pair of containment flaps in at least one structural feature, said structural feature being flap active portion longitudinal position, the first flap active portion longitudinal position being further forward than the second flap active portion longitudinal position; and
  simultaneously offering for sale the first and second disposable absorbent articles.

7. The method of marketing gender-specific absorbent articles of claim 6 wherein the articles are pant-like adult incontinence articles.

8. The method of marketing gender-specific absorbent articles of claim 6, wherein the first pair of containment flaps differs from the second pair of containment flaps in at least two structural features.

9. The method of marketing gender-specific absorbent articles of claim 6 wherein the first article is contained in a first package and the second article is a contained in a second package, wherein the first package includes indicia which denotes that the first article is adapted for use by males, and the second package includes indicia which denotes that the second article is adapted for use by females.

10. The method of marketing gender-specific absorbent articles of claim 9, wherein the indicia on the first package denotes that the first article is uniquely adapted to address protection issues for males, and the indicia on the second package denotes that the second article is uniquely adapted to address protection issues for females.

11. The method of marketing gender-specific absorbent articles of claim 6, comprising the additional step of providing a message embodied in a tangible medium that refers to the first and second disposable absorbent articles and that indicates that the first disposable absorbent article is adapted for use by males and that the second disposable absorbent article is adapted for use by females.

12. An array of gender-specific disposable absorbent articles, the array comprising a first disposable absorbent article adapted to be worn by males and a second disposable absorbent article adapted to be worn by females,
  wherein the first article comprises:
    a chassis comprising a garment-side outer cover, a bodyside liner, and an absorbent core sandwiched between the outer cover and liner, the chassis defining a front portion, a back portion, a crotch portion connecting the front and back portions, a front waist edge, a back waist edge, two side edges connecting the front and back waist edges,
    wherein the chassis has a leg-opening front edge establishing a boundary having a first convexity, a leg-opening side edge, a leg-opening back edge establishing a first concavity; a waist-opening front edge, and a first crotch width, and wherein the absorbent core has a front edge, a side edge, a first frontal area, and a first frontal transverse span;
    wherein said first article has a first anterior length equaling the shortest distance between the leg-opening front edge and the waist opening front edge; a first gasket width; and a first waist/absorbent distance equaling the shortest distance between the front edge of the absorbent core and the waist-opening front edge;
    said first article further comprising a first pair of containment flaps disposed on the chassis, each flap defining a proximal end and a distal end and each flap having a first flap active length, a first flap active portion longitudinal position, a first flap tension, and a first flap height, each pair of flaps defining a first distal-to-distal spacing and a first proximal-to-proximal spacing;
  wherein the second article comprises:
    a chassis comprising a garment-side outer cover, a bodyside liner, and an absorbent core sandwiched between the outer cover and liner, the chassis defining a front portion, a back portion, a crotch portion connecting the front and back portions, a front waist edge, a back waist edge, two side edges connecting the front and back waist edges,
    wherein the chassis has a leg-opening front edge establishing a boundary having a second convexity, a leg-opening side edge, a leg-opening back edge establishing a boundary having a second concavity; a waist-opening front edge, and a second crotch width, and wherein the absorbent core has a front edge, a side edge, a second frontal area, and a second frontal transverse span;

wherein said second article has a second anterior length equaling the shortest distance between the leg-opening front edge and the waist opening front edge; a second gasket width; and a second waist/absorbent distance equaling the shortest distance between the front edge of the absorbent core and the waist-opening front edge;

said second article further comprising a second pair of containment flaps disposed on the chassis, each flap defining a proximal end and a distal end and each flap having a second flap active length, a second flap active portion longitudinal position, a second flap tension, and a second flap height, each pair of flaps defining a second distal-to-distal spacing and a second proximal-to-proximal spacing, wherein the first article differs from the second article in at least one fit feature, the differing fit feature selected from the group consisting of: the first anterior length being longer than the second anterior length, the first gasket width being greater than the second gasket width, the first waist/absorbent distance being less than the second waist/absorbent distance, the first convexity being less than the second convexity, the first concavity being less than the second concavity, the first frontal area being more than the second frontal area, and the first frontal transverse span being greater than the second frontal transverse span, and wherein the first pair of containment flaps differs from the second pair of containment flaps in at least one structural feature.

13. The array of gender-specific absorbent articles of the claim 12, wherein the structural feature is selected from the group consisting of: flap active length, flap active portion longitudinal position, flap tension, flap height, distal-to-distal spacing, and proximal-to-proximal spacing.

14. The array of gender-specific absorbent articles of claim 12, wherein the difference in structural feature between the first pair of containment flaps and the second pair of containment flaps is selected from the group consisting of: the first active flap length being greater than the second flap active length, the first flap longitudinal position being further forward than the second flap longitudinal position, the first flap tension being lower than the second flap tension, the first flap height being greater than the second flap height, the first distal-to-distal spacing being greater than the second distal-to-distal spacing, and the first proximal-to-proximal spacing being greater than the second proximal-to-proximal spacing.

15. The array of gender-specific absorbent articles of claim 14 wherein the articles are pant-like adult incontinence articles.

16. The array of gender specific absorbent articles of claim 12 wherein the first article is contained in a first package and the second article is a contained in a second package, wherein the first package includes indicia which denotes that the first article is adapted for use by males, and the second package includes indicia which denotes that the second article is adapted for use by females.

* * * * *